United States Patent
Xiang et al.

(10) Patent No.: US 9,360,476 B2
(45) Date of Patent: Jun. 7, 2016

(54) MICROFLUIDIC SYSTEM AND METHOD TO TEST FOR TARGET MOLECULES IN A BIOLOGICAL SAMPLE

(75) Inventors: Qing Xiang, Scarborough (CA); Warren Che Wor Chan, Toronto (CA); Jesse M. Klostranec, Toronto (CA)

(73) Assignee: FIO CORPORATION, Toronto (CA)

( * ) Notice: Subject to any disclaimer, the term of this patent is extended or adjusted under 35 U.S.C. 154(b) by 1481 days.

(21) Appl. No.: 12/520,295

(22) PCT Filed: Dec. 19, 2007

(86) PCT No.: PCT/CA2007/002317
§ 371 (c)(1),
(2), (4) Date: Feb. 11, 2010

(87) PCT Pub. No.: WO2008/074146
PCT Pub. Date: Jun. 26, 2008

(65) Prior Publication Data
US 2010/0151443 A1    Jun. 17, 2010

(30) Foreign Application Priority Data

Dec. 19, 2006 (CA) ........................... 2571904
Mar. 2, 2007 (CA) ........................... 2580589

(51) Int. Cl.
*B82Y 15/00* (2011.01)
*G01N 33/543* (2006.01)
(Continued)

(52) U.S. Cl.
CPC .......... *G01N 33/54366* (2013.01); *B82Y 15/00* (2013.01); *G01N 21/645* (2013.01);
(Continued)

(58) Field of Classification Search
CPC ................. G01N 33/54366; G01N 33/54346; G01N 33/587; G01N 33/588; G01N 21/645
USPC .......... 422/403, 413, 417, 73, 77, 82.05, 503, 422/504, 518, 527, 554; 435/7.1, 32, 34, 435/39, 285.2, 286.5, 287.2, 288.5, 288.7; 436/517, 518, 523, 528, 532, 533, 546, 436/10, 52, 56, 171, 172
See application file for complete search history.

(56) References Cited

U.S. PATENT DOCUMENTS 5,244,630 A    9/1993    Khalil et al.
5,662,824 A    9/1997    Sang et al.
(Continued)

FOREIGN PATENT DOCUMENTS

CA    2061574    8/1992
CA    2021587    4/2003
(Continued)

OTHER PUBLICATIONS

Chabinyc et al. An Integrated Fluorescence Detection System in Poly(dimethylsiloxane) for Microfluidic Application, Anal.Chem. 73: 4491-4498 (2001).*
(Continued)

*Primary Examiner* — Gail R Gabel
(74) *Attorney, Agent, or Firm* — DLA Piper LLP (US)

(57) ABSTRACT

A system and method to test for the presence of target molecules in a biological test sample includes test molecules, a microfluidic chip, and irradiating and detection devices. The test molecules include bio-recognition molecules conjugable with the target molecules, and the corresponding conjugates. The microfluidic chip includes sample channels and flow focusing channels adjoining the sample channels. A buffer exiting from the focusing channels directs a single-file stream of the test molecules through one of the sample channels. The irradiating device delivers radiation for absorption by the test molecules in the single-file stream. After absorption, the test molecules emit fluorescence of a distinct fluorescent spectrum for each of the conjugates. The detection device monitors identifies the presence of the conjugates by monitoring for the distinct fluorescent spectrum. Thus, the test system and method identifies the presence of the target molecules in the test sample.

46 Claims, 25 Drawing Sheets

(51) Int. Cl.
*G01N 21/64* (2006.01)
*G01N 33/58* (2006.01)

(52) U.S. Cl.
CPC ........ *G01N33/54346* (2013.01); *G01N 33/587* (2013.01); *G01N 33/588* (2013.01); *G01N 2021/6421* (2013.01); *G01N 2021/6441* (2013.01)

(56) References Cited

U.S. PATENT DOCUMENTS

| | | |
|---|---|---|
| 5,714,390 A | 2/1998 | Hallowitz et al. |
| 5,786,219 A | 7/1998 | Zhang et al. |
| 5,817,458 A | 10/1998 | King et al. |
| 5,837,442 A | 11/1998 | Tsang |
| 6,011,252 A | 1/2000 | Jensen |
| 6,022,500 A | 2/2000 | John et al. |
| 6,066,243 A | 5/2000 | Anderson et al. |
| 6,100,541 A | 8/2000 | Nagle et al. |
| 6,103,379 A | 8/2000 | Margel et al. |
| 6,114,038 A | 9/2000 | Castro et al. |
| 6,119,953 A | 9/2000 | Ganan-Calvo et al. |
| 6,120,666 A * | 9/2000 | Jacobson et al. ............. 204/452 |
| 6,172,193 B1 | 1/2001 | Primi et al. |
| 6,174,469 B1 | 1/2001 | Ganan-Calvo |
| 6,261,779 B1 | 7/2001 | Barbera-Guillem et al. |
| 6,274,323 B1 | 8/2001 | Bruchez et al. |
| 6,309,701 B1 | 10/2001 | Barbera-Guillem |
| 6,316,781 B1 | 11/2001 | Nagle et al. |
| 6,319,607 B1 | 11/2001 | Barbera-Guillem et al. |
| 6,333,110 B1 | 12/2001 | Barbera-Guillem |
| 6,340,588 B1 | 1/2002 | Nova et al. |
| 6,353,475 B1 | 3/2002 | Jensen et al. |
| 6,357,670 B2 | 3/2002 | Ganan-Calvo |
| 6,399,952 B1 | 6/2002 | Maher et al. |
| 6,409,900 B1 | 6/2002 | Parce et al. |
| 6,413,401 B1 | 7/2002 | Chow et al. |
| 6,430,512 B1 | 8/2002 | Gallagher |
| 6,468,808 B1 | 10/2002 | Nie et al. |
| 6,494,830 B1 | 12/2002 | Wessel |
| 6,498,353 B2 | 12/2002 | Nagle et al. |
| 6,504,607 B2 | 1/2003 | Jensen et al. |
| 6,506,609 B1 | 1/2003 | Wada et al. |
| 6,514,399 B1 | 2/2003 | Parce et al. |
| 6,524,793 B1 | 2/2003 | Chandler et al. |
| 6,528,165 B2 | 3/2003 | Chandler |
| 6,544,732 B1 | 4/2003 | Chee et al. |
| 6,548,171 B1 | 4/2003 | Barbera-Guillem et al. |
| 6,548,264 B1 | 4/2003 | Tan et al. |
| 6,554,202 B2 | 4/2003 | Ganan-Calvo |
| 6,576,155 B1 | 6/2003 | Barbera-Guillem |
| 6,592,821 B1 | 7/2003 | Wada et al. |
| 6,592,822 B1 | 7/2003 | Chandler |
| 6,630,307 B2 | 10/2003 | Bruchez et al. |
| 6,632,655 B1 | 10/2003 | Mehta et al. |
| 6,649,138 B2 | 11/2003 | Adams et al. |
| 6,673,662 B2 | 1/2004 | Singh |
| 6,680,211 B2 | 1/2004 | Barbera-Guillem et al. |
| 6,699,723 B1 | 3/2004 | Weiss et al. |
| 6,720,411 B2 | 4/2004 | Mirkin et al. |
| 6,734,420 B2 | 5/2004 | Empedocles et al. |
| 6,740,491 B2 | 5/2004 | Mirkin et al. |
| 6,752,966 B1 | 6/2004 | Chazan |
| 6,759,235 B2 | 7/2004 | Empedocles et al. |
| 6,767,706 B2 | 7/2004 | Quake et al. |
| 6,772,070 B2 | 8/2004 | Gilmanshin et al. |
| 6,773,812 B2 | 8/2004 | Chandler et al. |
| 6,778,724 B2 | 8/2004 | Wang et al. |
| 6,787,088 B2 | 9/2004 | Parce et al. |
| 6,835,326 B2 | 12/2004 | Barbera-Guillem |
| 6,872,249 B2 | 3/2005 | Peng et al. |
| 6,881,537 B1 | 4/2005 | Goudsmit et al. |
| 6,881,821 B2 | 4/2005 | Simmonds et al. |
| 6,890,764 B2 | 5/2005 | Chee et al. |
| 6,905,885 B2 | 6/2005 | Colsten et al. |
| 6,966,880 B2 | 11/2005 | Boecker et al. |
| 6,978,212 B1 | 12/2005 | Sunshine |
| 6,986,837 B2 | 1/2006 | Chow et al. |
| 7,037,729 B2 | 5/2006 | Nie et al. |
| 7,041,362 B2 | 5/2006 | Barbera-Guillem |
| 7,069,191 B1 | 6/2006 | Moore |
| 7,077,328 B2 | 7/2006 | Krichnaswamy et al. |
| 7,079,241 B2 | 7/2006 | Empedocles et al. |
| 7,166,475 B2 | 1/2007 | Colyer et al. |
| 7,171,983 B2 | 2/2007 | Chien et al. |
| 7,192,785 B2 | 3/2007 | Nie et al. |
| 7,243,670 B2 | 7/2007 | Witt et al. |
| 7,252,928 B1 | 8/2007 | Hafeman et al. |
| 7,267,799 B1 | 9/2007 | Borich et al. |
| 7,294,503 B2 * | 11/2007 | Quake et al. ............... 435/288.5 |
| 2001/0027918 A1 | 10/2001 | Parce et al. |
| 2001/0028055 A1 | 10/2001 | Fafard et al. |
| 2001/0046602 A1 | 11/2001 | Chandler et al. |
| 2001/0055764 A1 | 12/2001 | Empedocles et al. |
| 2002/0009728 A1 | 1/2002 | Bittner et al. |
| 2002/0022273 A1 | 2/2002 | Empedocles et al. |
| 2002/0031783 A1 | 3/2002 | Empedocles et al. |
| 2002/0037499 A1 | 3/2002 | Quake et al. |
| 2002/0045045 A1 | 4/2002 | Adams et al. |
| 2002/0048425 A1 | 4/2002 | McBride et al. |
| 2002/0051971 A1 | 5/2002 | Stuelpnagel et al. |
| 2002/0059030 A1 | 5/2002 | Otworth et al. |
| 2002/0066401 A1 | 6/2002 | Peng et al. |
| 2002/0118355 A1 | 8/2002 | Worthington et al. |
| 2002/0144644 A1 | 10/2002 | Zehnder et al. |
| 2002/0164271 A1 | 11/2002 | Ho |
| 2002/0182609 A1 | 12/2002 | Arcot |
| 2003/0003441 A1 | 1/2003 | Colston et al. |
| 2003/0017264 A1 | 1/2003 | Treadway et al. |
| 2003/0026740 A1 | 2/2003 | Staats |
| 2003/0073086 A1 | 4/2003 | Guire et al. |
| 2003/0099940 A1 | 5/2003 | Empedocles et al. |
| 2003/0132538 A1 | 7/2003 | Chandler |
| 2003/0148530 A1 | 8/2003 | Lauks |
| 2003/0148544 A1 | 8/2003 | Nie et al. |
| 2003/0157327 A1 | 8/2003 | Barbera-Guillem et al. |
| 2003/0165951 A1 | 9/2003 | Bruchez, Jr. et al. |
| 2003/0170613 A1 | 9/2003 | Straus et al. |
| 2003/0172043 A1 | 9/2003 | Guyon et al. |
| 2003/0175773 A1 | 9/2003 | Chee et al. |
| 2003/0176183 A1 | 9/2003 | Drucker et al. |
| 2003/0177038 A1 | 9/2003 | Rao |
| 2003/0177941 A1 | 9/2003 | Barbera-Guillem |
| 2003/0190628 A1 | 10/2003 | Nakao et al. |
| 2003/0194350 A1 | 10/2003 | Stamatelos et al. |
| 2004/0009341 A1 | 1/2004 | Naasani |
| 2004/0067485 A1 | 4/2004 | Mayes et al. |
| 2004/0072428 A1 | 4/2004 | Sato et al. |
| 2004/0096363 A1 | 5/2004 | Porter |
| 2004/0101621 A1 | 5/2004 | Adams et al. |
| 2004/0106218 A1 | 6/2004 | Wang et al. |
| 2004/0118684 A1 | 6/2004 | Wainright et al. |
| 2004/0147031 A1 | 7/2004 | Nakao |
| 2004/0176704 A1 | 9/2004 | Stevens et al. |
| 2004/0203170 A1 | 10/2004 | Barbera-Guillem |
| 2004/0204633 A1 | 10/2004 | Rentea et al. |
| 2004/0229261 A1 | 11/2004 | Young |
| 2004/0241424 A1 | 12/2004 | Barbera-Guillem |
| 2004/0241752 A1 | 12/2004 | Anderson et al. |
| 2004/0247861 A1 | 12/2004 | Naasani |
| 2004/0248167 A1 | 12/2004 | Quake et al. |
| 2004/0266022 A1 | 12/2004 | Sundararajan et al. |
| 2004/0267568 A1 | 12/2004 | Chandler et al. |
| 2005/0004346 A1 | 1/2005 | Dziegiel et al. |
| 2005/0009002 A1 | 1/2005 | Chen et al. |
| 2005/0011764 A1 | 1/2005 | Berndt et al. |
| 2005/0014134 A1 | 1/2005 | West et al. |
| 2005/0032047 A1 | 2/2005 | Simmonds et al. |
| 2005/0043894 A1 | 2/2005 | Fernandez et al. |
| 2005/0059030 A1 | 3/2005 | Bao et al. |
| 2005/0071199 A1 | 3/2005 | Riff |
| 2005/0106257 A1 | 5/2005 | Albayrak |
| 2005/0112277 A1 | 5/2005 | Banerjee et al. |
| 2005/0120946 A1 | 6/2005 | Hines et al. |

(56) References Cited

U.S. PATENT DOCUMENTS

| | | | |
|---|---|---|---|
| 2005/0128479 A1 | 6/2005 | Gilbert et al. | |
| 2005/0164264 A1 | 7/2005 | Shipwash | |
| 2005/0214536 A1 | 9/2005 | Schrier et al. | |
| 2005/0221296 A1 | 10/2005 | Simmonds et al. | |
| 2005/0227370 A1 | 10/2005 | Ramel et al. | |
| 2005/0239118 A1 | 10/2005 | Goudsmit et al. | |
| 2006/0008921 A1 | 1/2006 | Daniels et al. | |
| 2006/0012784 A1 | 1/2006 | Ulmer | |
| 2006/0014040 A1 | 1/2006 | Peng et al. | |
| 2006/0019098 A1 | 1/2006 | Chan et al. | |
| 2006/0029267 A1 | 2/2006 | Frost et al. | |
| 2006/0046330 A1 | 3/2006 | Chen et al. | |
| 2006/0063160 A1 | 3/2006 | West et al. | |
| 2006/0068203 A1 | 3/2006 | Ying et al. | |
| 2006/0078490 A1 | 4/2006 | Shih et al. | |
| 2006/0105335 A1 | 5/2006 | Daehne et al. | |
| 2006/0152372 A1 | 7/2006 | Stout | |
| 2006/0169800 A1 | 8/2006 | Rosell | |
| 2006/0173715 A1 | 8/2006 | Wang | |
| 2006/0194030 A1 | 8/2006 | Barbera-Guillem | |
| 2007/0020779 A1 | 1/2007 | Stavis et al. | |
| 2007/0031283 A1 | 2/2007 | Davis et al. | |
| 2007/0042406 A1 | 2/2007 | Yantz et al. | |
| 2007/0081920 A1 | 4/2007 | Murphy et al. | |
| 2007/0128083 A1 | 6/2007 | Yantz et al. | |
| 2007/0161043 A1 | 7/2007 | Nie et al. | |
| 2010/0021937 A1* | 1/2010 | Greenberg et al. | 435/7.2 |

FOREIGN PATENT DOCUMENTS

| | | |
|---|---|---|
| CA | 2518352 | 3/2005 |
| EP | 1315099 | 5/2003 |
| JP | 2002-271 | 1/2002 |
| JP | 2005-508493 | 3/2005 |
| WO | 99/19000 | 4/1999 |
| WO | 99/36564 | 7/1999 |
| WO | 99/64840 | 12/1999 |
| WO | 99/66318 | 12/1999 |
| WO | 00/13580 | 3/2000 |
| WO | 00/28598 | 5/2000 |
| WO | 00/70080 | 11/2000 |
| WO | 01/20533 | 3/2001 |
| WO | 01/89585 | 11/2001 |
| WO | 01/93754 | 12/2001 |
| WO | 02/04484 | 1/2002 |
| WO | 03/003015 | 1/2003 |
| WO | 2004/008550 | 1/2004 |
| WO | 2004/040319 | 5/2004 |
| WO | 2005/023923 | 3/2005 |
| WO | 2005/031802 | 4/2005 |
| WO | 2005/052996 | 6/2005 |
| WO | 2005/053649 | 6/2005 |
| WO | 2005/061095 | 7/2005 |
| WO | 2006/033732 | 3/2006 |
| WO | 2006/045004 | 4/2006 |
| WO | 2006/072306 | 7/2006 |
| WO | 2006/132953 | 12/2006 |
| WO | 2007/011622 | 1/2007 |
| WO | 2008/089155 | 7/2008 |
| WO | 2008/147382 | 12/2008 |
| WO | 2009/059404 | 5/2009 |

OTHER PUBLICATIONS

Lawrence et al. A Comparison of Avalanche Photodiode and Photomultiplier Tube Detectors for Flow Cytometry, Proc. of SPIE vol. 6859, 6859OM-1-11 (2008).*

Han et al. Quantum-dot-tagged microbeads for multiplexed optical coding of biomolecules, Nature Biotechnology 19: 631-635 (Jul. 2001).*

Alivisatos, A.P., Perspectives on the Physical Chemistry of Semiconductor Nanocrystals, Journal of Physical Chemistry, 1996, pp. 13226-13239, vol. 100, No. 31, American Chemical Society, USA.

Bakalova, Rurniana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.

Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.

Branch, Mary Ann et al., A Subspace, Interior, and Conjugate Gradient Method for Large-Scale Bound-Constrained Minimization Problems, SIAM J. Sci. Comput., Aug. 3, 1999, pp. 1-23, vol. 21, No. 1, Society for Industrial and Applied Mathematics.

Bruchez, Marcel Jr. et al., Semiconductor Nanocrystals as Fluorescent Biological Labels, Science, Sep. 25, 1998, pp. 2013-2015, vol. 281, American Association for the Advancement of Science, USA.

Burns, Mark A. et al., An Integrated Nanoliter DNA Analysis Device, Science, Oct. 16, 1998, pp. 484-487, vol. 282, No. 5388, American Association for the Advancement of Science, USA.

Chabinyc, Michael L. et al., An Integrated Fluorescence Detection System in Poly(dimethylsiloxane) for Microfluidic Applications, Analytical Chemistry, Sep. 15, 2001, pp. 4494-4498, vol. 73, No. 18, American Chemical Society, USA.

Chan, Eugene Y. et al., DNA Mapping Using Microfluidic Stretching and Single-Molecule Detection of Fluorescent Site-Specific Tags, Genome Research, 2004, pp. 1137-1146, vol. 14, Cold Spring Harbour Laboratory Press, USA.

Chan, Warren C.W. et al., Luminescent quantum dots for multiplexed biological detection and imaging, Current Opinion in Biotechnology, 2002, pp. 40-46, vol. 13, Elsevier Science Ltd.

Chan, Warren C.W. et al., Quantum Dot Bioconjugates for Ultrasensitive Nonisotopic Detection, Science, Sep. 25, 1998, pp. 2016-2018, vol. 281, American Association for the Advancement of Science, USA.

Chou, Hou-Pu et al., A microfabricated device for sizing and sorting DNA molecules, PNAS—Proceedings of the National Academy of Sciences of the United States of America, Jan. 1999, pp. 11-13, vol. 96, The National Academy of Sciences, USA, only p. 13 provided/reviewed.

Dabbousi, B.O. et al., (CdSe)ZnS Core-Shell Quantum Dots: Synthesis and Characterization of a Size Series of Highly Luminescent Nanocrystallites, Journal of Physical Chemistry B, 1997, pp. 9463-9475, vol. 101, No. 46, American Chemical Society, USA.

Duffy, D.C. et al., Rapid Prototyping of Microfluidic Systems in Poly(dimethylsiloxane), Analytical Chemistry, Dec. 1, 1998, pp. 4974-4984, vol. 70, No. 23, American Chemical Society, USA.

Eisenstein, Michael, Technology Feature: Protein Arrays—Growing pains, Losing the Label, an Apt Solution? & (Almost) No Assembly Required, Nature, Dec. 14, 2006, pp. 959-962, vol. 444, Nature Publishing Group, USA.

Fournier-Bidoz, Sebastien et al., Facile and Rapid One-Step Mass Preparation of Quantum-Dot Barcodes, Angewandte Chemie International Edition, 2008, pp. 5577-5581, vol. 47, No. 30, Wiley-VCH Verlag GmbH & Co. KGaA, Weinheim.

Fu, Anne Y. et al., A microfabricated fluorescence-activated cell sorter, Nature Biotechnology, Nov. 1999, pp. 1109-1111, vol. 17, Nature America Inc., USA.

Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.

Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.

Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.

Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.

Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.

(56) References Cited

OTHER PUBLICATIONS

Gershon, Diane, Technology Feature: DNA Microarrays—More than than gene expression, It's a Small World, Microassays Move Downstream & On the Hardware Front, Nature, Oct. 20, 2005, pp. 1195-1198, vol. 437, Nature Publishing Group, USA.

Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.

Grumann, M. et al., Parallelization of Chip-Based Fluorescence Immuno-Assays with Quantum-Dot Labelled Beads, The 13th International Conference on Solid-State Sensors, Actuators and Microsystems, Jun. 2005, pp. 1114-1117, IEEE.

Han, Mingyong et al., Quantum-dot-tagged microbeads for multiplexed optical coding of biomolecules, Nature Biotechnology, Jul. 2001, pp. 631-635, vol. 19, Nature Publishing Group, USA.

Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.

Kloepfer, Jeremiah A. et al., Photophysical Properties of Biologically Compatible CdSe Quantum Dot Structures, Journal of Physical Chemistry B, 2005, pp. 9996-10003, vol. 109, No. 20, American Chemical Society, USA.

Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.

Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.

Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.

Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.

Malamud, D. et al., Point Detection of Pathogens in Oral Samples, Adv Dent Res, Jun. 2005, pp. 12-16, vol. 18.

Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.

Mattoussi, H. et al., Luminescent Quantum Dot-Bioconjugates in Immunoassays, FRET, Biosensing, and Imaging Applications, JALA—Journal of the Association for Laboratory Automation, Feb. 2004, pp. 28-32, vol. 9, No. 1, The Association for Laboratory Automation, USA.

Medintz, Igor L. et al., Quantum dot bioconjugates for imaging, labelling and sensing, Nature Materials, Jun. 2005, pp. 435-446, vol. 4, Nature Publishing Group, USA.

Moré, Jorge J. et al., Computing a Trust Region Step, SIAM J. Sci. Stat. Comput., Sep. 1983, pp. 553-572, vol. 4, No. 3, Society for Industrial and Applied Mathematics.

Murray, C.B. et al., Synthesis and Characterization of Nearly Monodisperse CdE (E=S, Se, Te) Semiconductor Nanocrystallites, Journal of the American Chemical Society, 1993, pp. 8706-8715, vol. 115, No. 19, American Chemical Society, USA.

Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.

Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.

Pregibon, Daniel C. et al., Multifunctional Encoded Particles for High-Throughput Biomolecule Analysis, Science, Mar. 9, 2007, pp. 1393-1396, vol. 315, American Association for the Advancement of Science, USA [downloaded on Mar. 9, 2009 from http://www.science mag.org].

Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, , vol. 78, No. 16, American Chemical Society, USA.

Service, Robert F., DNA Analysis: Microchip Arrays Put DNA on the Spot, Science, Oct. 16, 1998, pp. 396-399, vol. 282, No. 5388, American Association for the Advancement of Science, USA [downloaded on Mar. 20, 2008 from http://www.science mag.org/cgi/content/full/282/5388/396].

Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.

Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.

Thomson, B. et al, Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.

Xu, Hongxia et al., Muliplexed SNP genotyping using the Qbead™ system: a quantum dot-encoded microsphere-based assay, Nucleic Acids Research, 2003, pp. 1-10, vol. 31, No. 8, Oxford University Press.

Xuan, Xiangchun et al., Focused electrophoretic motion and selected electrokinetic dispensing of particles of particles and cells in cross-microchannels, Electrophoresis, 2005, pp. 3552-3560, vol. 26, Wiley-VCH Verlag GmbH & co. KGaA, Weinheim.

Yun, Kwang-Seok et al., A microfluidic chip for measurement of biomolecules using a microbead-based quantum dot fluorescence assay, Measurement Science and Technology, 2006, pp. 3178-3183, vol. 17, IOP Publishing Ltd, UK.

Zaytseva, Natalya V. et al., Development of a microfluidic biosensor module for pathogen detection, Lab on a Chip, Jul. 6, 2005, pp. 805-811, vol. 5, The Royal Society of Chemistry.

International Search Report and Written Opinion from PCT/CA2007/002317 mailed Apr. 17, 2008.

International Preliminary Report on Patentability from PCT/CA2007/002317 dated Oct. 17, 2008.

\* cited by examiner

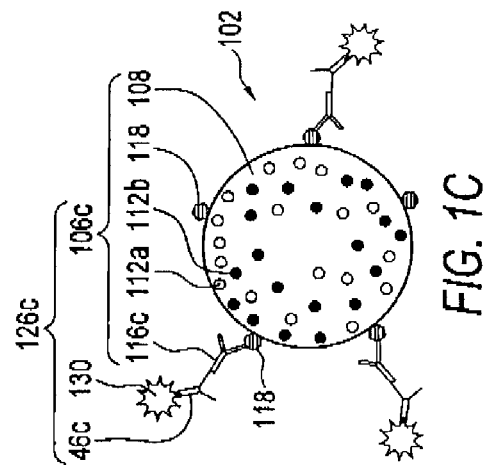
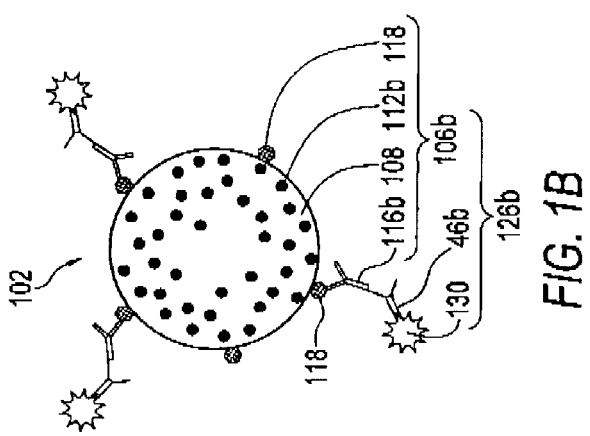
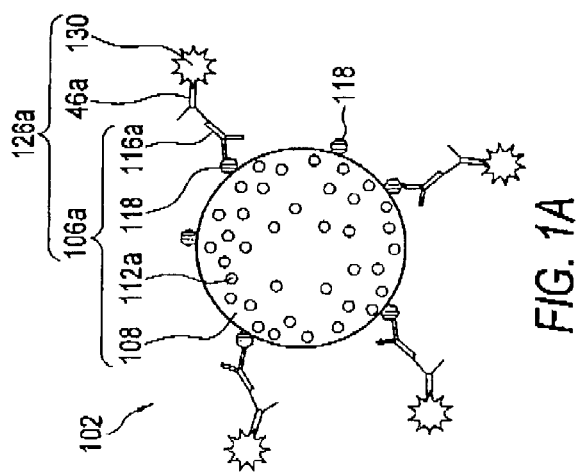

| | Sample | Ag HBV | Ag HIV | Ag HCV | Ab HBV | Ab HIV | Ab HCV | AlexaFluor-488 anti-IgG | Notes |
|---|---|---|---|---|---|---|---|---|---|
| 2 Pathogen Multiplex | HBV+,HIV+ | + | + | N/A | + | + | N/A | + | 2 Ab |
| | HBV+,HIV- | + | + | N/A | + | - | N/A | + | 1 Ab |
| | HBV-,HIV+ | + | - | N/A | - | + | N/A | + | Cross-reactivity |
| | HBV-,HIV- | + | + | N/A | + | + | N/A | + | |
| | Control 1 | - | + | N/A | - | - | N/A | + | No Ab |
| | Control 2 | + | - | N/A | + | + | N/A | + | No Ag |
| | Control 3 | - | + | N/A | - | + | N/A | + | |
| | Control 4 | + | + | N/A | + | + | N/A | - | No Dye |
| 3 Pathogen Multiplex | HBV+,HIV+,HCV+ | + | + | + | + | + | + | + | 3 Ab |
| | HBV-,HIV+,HCV+ | + | + | + | + | + | - | + | 2 Ab |
| | HBV+,HIV-,HCV+ | + | - | - | + | - | + | + | |
| | HBV+,HIV+,HCV- | - | - | - | + | + | + | + | Cross-reactivity |
| | Control 1 | + | - | + | - | + | - | + | |
| | Control 2 | - | + | - | + | - | + | + | |
| | Control 3 | + | + | - | - | + | - | + | |
| | Control 4 | - | - | - | + | - | + | + | |
| | Control 5 | - | + | - | + | + | - | + | No Ab |
| | Control 6 | + | - | + | - | + | - | + | No Ag |
| | | + | + | + | + | + | + | - | No Dye |

FIG. 12

MICROFLUIDIC SYSTEM AND METHOD TO TEST FOR TARGET MOLECULES IN A BIOLOGICAL SAMPLE

FIELD OF THE INVENTION

The present invention relates to the field of microfluidics. In particular, it relates to a microfluidic channel structure for reading fluorescent microbeads.

BACKGROUND OF THE INVENTION

The last decade has seen many advances in the fields of microtechnology and nanotechnology. One of the challenges created by these advances is developing practical uses for discovered scientific phenomena.

A few published reports of attempts to integrate nano- with microtechnology for biomolecular or viral detection have been described [W. Liu et al., Lab Chip, 5, 1327 (2005); K. Yun, D. Lee, H. Kim, E. Yoon, Meas. Sci. Technol., 17, 3178 (2006); J. Steigert et al., JALA, 10, 331 (2005)]. In these studies, the researchers used a combination of nanoparticles, microbeads, and microfluidics for detection. In all cases, the detection sensitivity was lower than desirable for a productive, commercial product. Furthermore, the analysis was not conducted in serum, which could decrease sensitivity because of interference from blood components [E. D. Goluch et al., Lab Chip, 6, 1293 (2006)].

Similarly, bio-barcodes using gold nanoparticles have been demonstrated for applications in genomic or proteomic diagnostics [J. Tate, G. Ward, Clin. Biochem. Rev., 25, 105 (2004); S. I. Stoeva, J. Lee, C. S. Thaxton, C. A. Mirkin, Angew. Chem. Int. Ed., 45, 3303 (2006); P. Mitchell, Nat. Biotech., 20, 225 (2002)]). In these methods, the detection strategy requires multiple steps to achieve assay detection as well as amplification to achieve good sensitivity. Thus, there is a need for a detection system that only requires a few steps and can achieve a reasonably high level of sensitivity.

Published United States Patent Application No. US2007/0020779 of Stavis et al. discloses a method of detecting quantum dots conjugates in a sub-micrometer fluidic channel. The cross-sectional size of the channels used in Stavis is on the order of 500 nm and the detected conjugates on the order of 5-10 nm. Furthermore, in order to achieve single conjugate detection, the concentration of the sample was reduced to the femtomolar level, increasing the difficulty of sample preparation and the limits on the detection system. An alternative and more efficient system and method of single conjugate detection, ideally for use with more easily handled microscale molecules, is needed.

Objects of this invention are preferably accomplished, but may not be necessarily as described, nor is it necessary for all objects to be accomplished by a single embodiment of the invention. Additional objects may be accomplished that are not listed herein.

It is an object of this invention to enable multiplexed detection of target molecules of one or more target types by irradiating and detecting fluorescent emission from a single-file stream of test molecules.

It is an object of this invention to enable testing of biological samples for infectious diseases. It is a further object to enable testing of specific biological samples of blood, serum, sputum and/or urine.

It is an object of this invention to enable multiplexed testing for infectious diseases in biological samples. It is a further object to enable multiplexed testing for Hepatitis B, Hepatitis C and HIV in any combination.

It is an object of this invention to provide an improved microfluidic channel structure that facilitates flow through the channels.

It is an object of this invention to provide a fixed-wavelength EMF radiation device, such as a 488 nm laser, as the irradiation device in a test system such that the incident EMF radiation and emitted fluorescence from the target molecule can travel along the same optical path prior to the emitted fluorescence entering the detection device.

It is an object of this invention to partially or completely fulfill one or more of the above-mentioned objects and to mitigate and/or ameliorate any disadvantages of the prior art, regardless of whether any such disadvantages are described herein.

SUMMARY OF THE INVENTION

In accordance with the present invention there is disclosed a test system for use with a buffer to test for the presence of target molecules of one or more target types in a biological test sample. The test system includes a first set of test molecules, a microfluidic chip, an irradiating device, and a detection device. The first set of test molecules is selected from a group that includes bio-recognition molecules (BRMs) and conjugates of the BRMs and the target molecules, if present in the test sample. The BRMs are of one or more BRM types. Each of the BRM types is conjugable with a respective one of the target types. The conjugates are of one or more conjugate types each corresponding to a different one of the BRM types in conjugation with its said respective one of the target types. The microfluidic chip includes a chip substrate portion that is shaped to define one or more elongate sample channels, and one or more flow focusing channels, therein. The sample channels are sized to enable passage therethrough of the test molecules. The flow focusing channels are for operative passage therethrough of the buffer. The one or more flow focusing channels adjoin the one or more elongate sample channels. The buffer exits from the flow focusing channels and operatively directs a single-file stream of the test molecules through at least one of the sample channels. The irradiating device operatively delivers electromagnetic frequency (EMF) radiation, at an irradiation position along the aforesaid at least one of the sample channels, for absorption by the test molecules in the single-file stream. The test molecules emit fluorescence after absorption of the EMF radiation. The fluorescence of the test molecules includes a distinct fluorescent spectrum for each one of the conjugate types. The detection device monitors the single-file stream for the fluorescence emitted by the test molecules. The detection device identifies the presence of the conjugates in the first set of test molecules by monitoring for the distinct fluorescent spectrum of each one of the conjugate types. In this manner, the test system identifies the presence of the target molecules in the test sample.

According to an aspect of one preferred embodiment of the invention, each of the BRMs includes a microbead tagged with one or more BRM fluorophores that are coupled to the microbead. The BRM fluorophores emit at least a BRM part of the fluorescence of the distinct fluorescent spectrum after absorption of the EMF radiation.

According to an aspect of one preferred embodiment of the invention, the BRM fluorophores include one or more quantum dots of one or more quantum dot types. The quantum dots together emit at least the BRM part of the fluorescence of the distinct fluorescent spectrum after absorption of the EMF radiation.

According to an aspect of one preferred embodiment of the invention, the quantum dots are of two or more of the quantum dot types.

According to an aspect of one preferred embodiment of the invention, the BRM fluorophores include one or more fluorescent dyes of one or more fluorescent dye types. The fluorescent dyes together emit at least the BRM part of the fluorescence of the distinct fluorescent spectrum after absorption of the EMF radiation.

According to an aspect of one preferred embodiment of the invention, the conjugates are less than about 10 micrometers (μm) in size, and preferably less than about 5 μm in size, and still more preferably, less than about 1 μm in size.

According to an aspect of one preferred embodiment of the invention, each of the conjugates further includes a target marker fluorophore bound to a respective one of the target molecules. The target marker fluorophore emits a target part of the fluorescence of the distinct fluorescent spectrum after absorption of the EMF radiation.

According to an aspect of one preferred embodiment of the invention, each of the BRMs includes a microbead tagged with one or more BRM fluorophores that are coupled to the microbead. Each of the conjugates further includes a target marker fluorophore bound to a respective one of the target molecules. For each of the conjugates, the BRM fluorophores emit a BRM part, and the target marker fluorophore emits a target part, of the fluorescence of the distinct fluorescent spectrum after absorption of the EMF radiation. As such, the BRM fluorophores and the target marker fluorophore together emit the fluorescence of the distinct fluorescent spectrum after absorption of the EMF radiation.

According to an aspect of one preferred embodiment of the invention, the detection device includes at least two avalanche photodetectors (APDs) monitoring the single-file stream for the fluorescence emitted by the test molecules. A first one of the APDs is adapted to receive and identify the presence of the BRM part, and a second one of the APDs adapted to receive and identify the presence of the target part, of the fluorescence of the distinct fluorescent spectrum for said each of the conjugates.

According to an aspect of one preferred embodiment of the invention, the target part has a lower intensity than the BRM part of the fluorescence of the distinct fluorescent spectrum for each of the conjugates. The second one of the APDs has a greater sensitivity than the first one of the APDs.

In accordance with the present invention there is disclosed another test system for use with a buffer to test for the presence of target molecules of one or more target types in a biological test sample. According to this embodiment of the invention, the test system is also for use with a first set of test molecules selected from a group that includes bio-recognition molecules (BRMs) and conjugates of the BRMs and the target molecules, if present in the test sample. The BRMs are of one or more BRM types. Each of the BRM types is conjugable with a respective one of the target types. The test molecules are such as to emit fluorescence after absorption of EMF radiation. The conjugates are of one or more conjugate types each corresponding to a different one of the BRM types in conjugation with its said respective one of the target types. According to this embodiment of the invention, the test system includes a microfluidic chip, an irradiating device, and a detection device. The microfluidic chip includes a chip substrate portion shaped to define one or more elongate sample channels, and one or more flow focusing channels, therein. The sample channels are sized to enable passage therethrough of the test molecules. The flow focusing channels are for operative passage therethrough of the buffer. The flow focusing channels adjoin the sample channels. The buffer exits from the flow focusing channels operatively directing a single-file stream of the test molecules through at least one of the sample channels. The irradiating device operatively delivers electromagnetic frequency (EMF) radiation, at an irradiation position along that aforesaid at least one of the sample channels, for absorption by the test molecules in the single-file stream. The fluorescence of the test molecules includes a distinct fluorescent spectrum for each one of the conjugate types. The detection device monitors the single-file stream for the fluorescence emitted by the test molecules. The detection device identifies the presence of the conjugates in the first set of test molecules by monitoring for the distinct fluorescent spectrum of each one of the conjugate types. In this manner, the test system identifies the presence of the target molecules in the test sample.

According to an aspect of one preferred embodiment of the invention, said at least one of the sample channels is defined by one or more elongate channel walls of the chip substrate portion. The channel walls include two opposing side channel portions. The buffer, exiting from the flow focusing channels, operatively directs the single-file stream of the test molecules along a sample path that is in spaced relation from at least the aforesaid two opposing side channel portions.

According to an aspect of one preferred embodiment of the invention, the microfluidic chip further includes a glass slide underlying the chip substrate portion. The glass slide defines a bottom channel portion of said at least one of the sample channels. The channel walls additionally include a top channel portion. The sample path is operatively in the aforesaid spaced relation from both the bottom channel portion and the top channel portion.

According to an aspect of one preferred embodiment of the invention, the aforesaid at least one of the sample channels includes a sample focused channel. The sample channels also include a sample supply channel in fluid communication with the sample focused channel. The sample focused channel is downstream of the flow focusing channels. As such, the buffer exiting from the flow focusing channels and the single-file stream of the test molecules operatively flow through the sample focused channel.

According to an aspect of one preferred embodiment of the invention, a buffer flow rate of the buffer, operatively flowing through the sample focused channel, is higher than a test flow rate of the test molecules in the single-file stream.

According to an aspect of one preferred embodiment of the invention, the flow focusing channels include at least two flow focusing channels, adjoining the sample channels upstream of the aforesaid at least one of the sample channels. The two flow focusing channels adjoin the sample channels from opposing sides of the aforesaid at least one of the sample channels.

According to an aspect of one preferred embodiment of the invention, the two flow focusing channels adjoin the sample channels at a common intersection portion.

According to an aspect of one preferred embodiment of the invention, the buffer exiting from the flow focusing channels operatively focuses the test molecules into the single-file stream by less than about 10 micrometers (μm) downstream of the common intersection portion.

According to an aspect of one preferred embodiment of the invention, each of the flow focusing channels adjoins the sample channels at an adjoining angle of about 90 degrees.

According to an aspect of another preferred embodiment of the invention, each of flow focusing channels adjoins the sample channels at an adjoining angle of about 45 degrees.

According to an aspect of one preferred embodiment of the invention, the chip substrate portion is fabricated from polydimethylsiloxane (PDMS).

According to an aspect of one preferred embodiment of the invention, passage of the test molecules through the aforesaid at least one of the sample channels is facilitated by electrokinetic flow.

According to an aspect of one preferred embodiment of the invention, the flow focusing channels are in fluid communication with the sample channels. The chip substrate portion is additionally shaped to define a buffer well, a sample well, and a terminal well. Each buffer well is adjacent to a buffer starting point of each one of the flow focusing channels. The sample well is adjacent to a sample starting point of the sample channels upstream of the flow focusing channels. The terminal well is adjacent to an end point of the aforesaid at least one of the sample channels downstream of the flow focusing channels. The test system also includes a sample well electrode, a buffer well electrode, and a terminal well electrode. The sample well electrode is operatively positioned in the sample well. Each buffer well electrode is operatively positioned in one aforesaid buffer well. The terminal well electrode is operatively positioned in the terminal well. The sample well electrode is operatively supplied with a first electrical potential of a first polarity. The terminal well electrode is operatively supplied with a second electrical potential of an opposing second polarity. Each buffer well electrode is operatively supplied with a third electrical potential of the first polarity.

According to an aspect of one preferred embodiment of the invention, the third electrical potential is higher than the first electrical potential.

According to an aspect of one preferred embodiment of the invention, a ratio of the third electrical potential relative to the first electrical potential is about 1.8:1 (9:5).

According to an aspect of one preferred embodiment of the invention, a test flow rate of the test molecules in the single-file stream is at least about 30 test molecules per minute, and preferably at least about 60 test molecules per minute, and still more preferably about 500 test molecules per minute.

In accordance with the present invention there is also disclosed a further test system to test for the presence of target molecules of one or more target types in a biological test sample. According to this embodiment of the invention, the test system is for use with a first set of test molecules selected from a group that includes bio-recognition molecules (BRMs) and conjugates of the BRMs and the target molecules, if present in the test sample. The BRMs are of one or more BRM types. Each of the BRM types is conjugable with a respective one of the target types. The conjugates are of one or more conjugate types, each corresponding to a different one of the BRM types in conjugation with its aforesaid respective one of the target types. The test system is also for use with a microfluidic chip that includes a chip substrate portion, which is shaped to define one or more elongate sample channels therein. The sample channels are sized to enable passage therethrough of the test molecules. A single-file stream of the test molecules passes through at least one of the sample channels. According to this embodiment of the invention, the test system includes an irradiating device and a detection device. The irradiating device operatively delivers electromagnetic frequency (EMF) radiation, at an irradiation position along the aforesaid at least one of the sample channels, for absorption by the test molecules in the single-file stream. The test molecules emit fluorescence after absorption of the EMF radiation. The fluorescence of the test molecules includes a distinct fluorescent spectrum for each one of the conjugate types. The detection device monitors the single-file stream for the fluorescence emitted by the test molecules. The detection device identifies the presence of the conjugates in the first set of test molecules by monitoring for the distinct fluorescent spectrum of each one of the conjugate types. In this manner, the test system identifies the presence of the target molecules in the test sample.

According to an aspect of one preferred embodiment of the invention, the irradiating device includes an LED which operatively emits the EMF radiation for absorption by the test molecules in the single-file stream.

According to an aspect of another preferred embodiment of the invention, the irradiating device includes a laser, which operatively emits the EMF radiation for absorption by the test molecules in the single-file stream.

According to an aspect of one preferred embodiment of the invention, the laser has an operating power of between about 2 milliwatts (mW) and about 50 milliwatts (mW), and more preferably, between about 20 milliwatts (mW) and about 25 milliwatts (mW).

According to an aspect of one preferred embodiment of the invention, the EMF radiation operatively delivered by the irradiating device has an EMF wavelength of about 488 nm.

According to an aspect of one preferred embodiment of the invention, the detection device includes at least three avalanche photodetectors (APDs) monitoring the single-file stream for the fluorescence emitted by the test molecules. Each of the APDs is adapted to receive and identify the presence of a different range of wavelengths in the fluorescence emitted by the test molecules.

According to an aspect of one preferred embodiment of the invention, a first one of the APDs is adapted to receive and identify the presence of a green range of wavelengths. A second one of the APDs is adapted to receive and identify the presence of a yellow range of wavelengths. A third one of the APDs is adapted to receive and identify the presence of a red range of wavelengths.

According to an aspect of another preferred embodiment of the invention, the aforesaid at least three APDs include at least four APDs. A first one of the APDs is adapted to receive and identify the presence of a green range of wavelengths. A second one of the APDs is adapted to receive and identify the presence of a yellow range of wavelengths. A third one of the APDs is adapted to receive and identify the presence of an orange range of wavelengths. A fourth one of the APDs is adapted to receive and identify the presence of a red range of wavelengths.

According to an aspect of yet another preferred embodiment of the invention, the at least three APDs include at least four APDs. A first one of the APDs is adapted to receive and identify the presence of a blue range of wavelengths. A second one of the APDs is adapted to receive and identify the presence of a green range of wavelengths. A third one of the APDs is adapted to receive and identify the presence of a yellow range of wavelengths. A fourth one of the APDs is adapted to receive and identify the presence of a red range of wavelengths.

According to an aspect of one preferred embodiment of the invention, the detection device includes a charge-coupled device monitoring the single-file stream for the fluorescence emitted by the test molecules.

According to an aspect of one preferred embodiment of the invention, the detection device includes at least two avalanche photodetectors (APDs) monitoring the single-file stream for the fluorescence emitted by the test molecules. Each of the APDs is adapted to receive and identify the presence of a different range of wavelengths in the fluorescence emitted by the test molecules. The detection device additionally includes a charge-coupled device monitoring the single-file stream for the fluorescence emitted by the test molecules. Still further, the detection device includes a switch means for switching between monitoring the single-file stream with either the APDs or the charge-coupled device.

According to an aspect of one preferred embodiment of the invention, the detection device includes at least one trip sensor monitoring the single-file stream for the fluorescence emitted by the test molecules. Each aforesaid trip sensor generates a digital signal corresponding to an intensity of the fluorescence.

According to an aspect of one preferred embodiment of the invention, each aforesaid trip sensor generates the digital signal only when the intensity of the fluorescence is in excess of a minimum intensity. Each aforesaid trip sensor has a different pre-determined said minimum intensity.

According to an aspect of one preferred embodiment of the invention, the test system also includes a fiber optic cable delivering the fluorescence to the detection device from substantially adjacent to the irradiation position along the aforesaid at least one of the sample channels.

According to an aspect of one preferred embodiment of the invention, the test system also includes a housing encasing the irradiating device and the detection device. The housing is sized and adapted for portable and point-of-care diagnostic use.

According to an aspect of one preferred embodiment of the invention, the housing is sized and adapted for hand-held use.

In accordance with the present invention there is still further disclosed yet another test system for use with a buffer to test for the presence of target molecules of one or more target types in a biological test sample. According to this embodiment of the invention, the test system is also for use with a first set of test molecules selected from a group that includes bio-recognition molecules (BRMs) conjugates of the BRMs and the target molecules, if present in the test sample. The BRMs are of one or more BRM types. Each of the BRM types is conjugable with a respective one of the target types. The conjugates are of one or more conjugate types, each corresponding to a different one of the BRM types in conjugation with its aforesaid respective one of the target types. The test system is additionally for use with an irradiating and detection device that is capable of delivering electromagnetic frequency (EMF) radiation for absorption by the test molecules. The test molecules are such as to emit fluorescence after absorption of the EMF radiation. The fluorescence of the test molecules includes a distinct fluorescent spectrum for each one of the conjugate types. The irradiation and detection device is also capable of monitoring for, and identifying, the conjugates by the presence of the distinct fluorescent spectrum for each one of the conjugate types. According to this embodiment of the invention, the test system includes a microfluidic chip having a chip substrate portion that is shaped to define one or more elongate sample channels, and one or more flow focusing channels, therein. The sample channels are sized to enable passage therethrough of the test molecules. The flow focusing channels are for operative passage therethrough of the buffer. The flow focusing channels adjoin the sample channels. The buffer exits from the flow focusing channels and operatively directs a single-file stream of the test molecules through at least one of the sample channels. The microfluidic chip is adapted to operatively receive the EMF radiation from the irradiating and detection device, at an irradiation position along the aforesaid at least one of the sample channels, for absorption by the test molecules in the single-file stream. The microfluidic chip is adapted to enable the irradiation and detection device to monitor the single-file stream for the fluorescence emitted by the test molecules. In this manner, the conjugates are operatively identifiable by the presence of the distinct fluorescent spectrum for each one of the conjugate types. As such, the presence of the target molecules in the test sample is operatively identifiable by the test system.

According to an aspect of one preferred embodiment of the invention, the test system is particularly adapted for use with one or more biological test samples selected from the group consisting of blood, urine, sputum, and serum.

According to an aspect of one preferred embodiment of the invention, the test system may be used for diagnosis of a disease state selected from the group consisting of bacterial disease states, viral disease states, fungal disease states, and vector-induced disease states.

According to an aspect of one preferred embodiment of the invention, the test system may be used for diagnosis of one or more infectious diseases.

According to an aspect of one preferred embodiment of the invention, the test system may be used for diagnosis of a condition selected from the group consisting of HIV, HBV and HCV.

According to an aspect of one preferred embodiment of the invention, the test system may be used for simultaneous diagnosis of two or more the conditions selected from the group consisting of HIV, HBV and HCV.

In accordance with the present invention there also disclosed a method of focusing molecules to facilitate a test for the presence of target molecules of one or more target types in a biological test sample. The method includes a sample flowing step, a buffer flowing step, and a sample focusing step after the buffer flowing step. In the sample flowing step, test molecules are passed through one or more elongate sample channels formed in a chip substrate portion of a microfluidic chip. In the buffer flowing step, a buffer is passed through one or more flow focusing channels formed in the chip substrate portion of the microfluidic chip. The flow focusing channels adjoin the one or more elongate sample channels. In the sample focusing step, a single-file stream of the test molecules is directed through at least one of the sample channels by passage of the buffer from the flow focusing channels into the one or more elongate sample channels.

According to an aspect of one preferred embodiment of the invention, the method also includes a test molecule-forming step before the sample flowing step. In the test molecule-forming step, the test molecules are formed by introducing bio-recognition molecules (BRMs) of one or more BRM types. Each of the BRM types is conjugable with a respective one of the target types. As such, the test molecules include conjugates of the BRMs and the target molecules, if present in the test sample.

According to an aspect of one preferred embodiment of the invention, in the test molecule-forming step, the conjugates are less than about 10 micrometers (μm) in size, and preferably less than about 5 μm in size, and still more preferably, less than about 1 μm in size.

According to an aspect of one preferred embodiment of the invention, in the test molecule-forming step, target marker fluorophores are introduced. The target marker fluorophores are conjugable with one or more of the target types. As such, the test molecules include conjugates of the BRMs, the target marker fluorophores, and the target molecules, if present in the test sample.

According to an aspect of one preferred embodiment of the invention, in the sample focusing step, the single-file stream of the test molecules is directed along a sample path that is in spaced relation from at least two opposing side channel portions of the aforesaid at least one of the sample channels.

According to an aspect of another preferred embodiment of the invention, in the sample focusing step, the single-file stream of the test molecules is directed along a sample path that is in spaced relation from at least top and bottom channel portions of the aforesaid at least one of the sample channels.

According to an aspect of one preferred embodiment of the invention, in the sample focusing step, the buffer flows into the aforesaid at least one of the sample channels at a buffer flow rate that is higher than a test flow rate of the test molecules in the single-file stream.

According to an aspect of one preferred embodiment of the invention, in the sample focusing step, at least two of the flow focusing channels adjoin the sample channels, from opposing sides thereof, upstream of said at least one of the sample channels.

According to an aspect of one preferred embodiment of the invention, in the sample focusing step, the two flow focusing channels adjoin the sample channels at a common intersection portion.

According to an aspect of one preferred embodiment of the invention, in the sample focusing step, each of the one or more flow focusing channels adjoins the sample channels at an adjoining angle of about 90 degrees.

According to an aspect of another preferred embodiment of the invention, in the sample focusing step, each of the one or more flow focusing channels adjoins the sample channels at an adjoining angle of about 45 degrees.

According to an aspect of one preferred embodiment of the invention, in the sample focusing step, passage of the single-file stream of the test molecules through the aforesaid at least one of the sample channels is facilitated by electrokinetic flow.

According to an aspect of one preferred embodiment of the invention, the method also includes an electrokinetic step before the sample focusing step. In the electrokinetic step, a first electrical potential of a first polarity is supplied to the sample channels upstream of the flow focusing channels. In the electrokinetic step, a second electrical potential of an opposing second polarity is supplied to the aforesaid at least one of the sample channels downstream of the flow focusing channels. In the electrokinetic step, a third electrical potential of the first polarity is supplied to each one of the flow focusing channels.

According to an aspect of one preferred embodiment of the invention, in the electrokinetic step, the third electrical potential is higher than the first electrical potential.

According to an aspect of one preferred embodiment of the invention, in the electrokinetic step, a ratio of the third electrical potential relative to the first electrical potential is about 1.8:1 (9:5).

According to an aspect of one preferred embodiment of the invention, in the test molecule-forming step, the conjugates are of one or more conjugate types, each corresponding to a different one of the BRM types in conjugation with its said respective one of the target types. The method also includes an irradiating step after the sample focusing step, a fluorescence-detecting step after the irradiating step, and a conjugate-identifying step after the irradiating step. In the irradiating step, electromagnetic frequency (EMF) radiation is delivered to the test molecules in the single-file stream. In the fluorescence-detecting step, the single-file stream is monitored for fluorescence emitted by the test molecules. Each of the conjugates, after absorption of the EMF radiation, emits fluorescence of a distinct fluorescent spectrum for each one of the conjugate types. In the conjugate-identifying step, the presence of the target molecules in the test sample is identified by monitoring for the distinct fluorescent spectrum of each one of the conjugate types.

According to an aspect of one preferred embodiment of the invention, in the test-molecule forming step, target marker fluorophores are bound to respective ones of the target molecules. As such, in the fluorescence-detecting step, the target marker fluorophores emit a target part of the distinct fluorescent spectrum for each one of the conjugate types. The method further includes a BRM-forming step, before the test-molecule forming step, of tagging a microbead with one or more BRM fluorophores that are coupled to the microbead. As such, in the fluorescence-detecting step, the BRM fluorophores emit a BRM part of the distinct fluorescent spectrum for each one of the conjugate types.

According to an aspect of one preferred embodiment of the invention, in the fluorescence-detecting step, fluorescence emitted by the conjugates is received by at least two avalanche photodetectors (APDs). A first one of the APDs receives and identifies the presence of the BRM part, and a second one of the APDs receives and identifies the presence of the target part, of the fluorescence of the distinct fluorescent spectrum for said each of the conjugates.

According to an aspect of one preferred embodiment of the invention, in the irradiating step, a laser having an operating power of between about 2 megawatts (mW) and about 50 milliwatts (mW) delivers the EMF radiation to the test molecules in the single-file stream. More preferably, the operating power is between about 20 milliwatts (mW) and about 25 milliwatts (mW).

According to an aspect of one preferred embodiment of the invention, in the irradiating step, the EMF radiation has an EMF wavelength of about 488 nm.

According to an aspect of one preferred embodiment of the invention, in the fluorescence-detecting step, the fluorescence emitted by the conjugates is received by a charge-coupled device.

According to an aspect of one preferred embodiment of the invention, in the fluorescence-detecting step, the fluorescence emitted by the conjugates is selectively received by at least one of a charge-coupled device and one or more avalanche photodetectors (APDs).

Other and further advantages and features of the invention will be apparent to those skilled in the art from the following detailed description thereof, taken in conjunction with the accompanying drawings.

BRIEF DESCRIPTION OF THE DRAWINGS

The invention will now be described in more detail, by way of example only, with reference to the accompanying drawings, in which like numbers refer to like elements, wherein:

FIG. 1A is an illustration of a first conjugate according to the present invention;

FIG. 1B is an illustration of a second conjugate according to the present invention;

FIG. 1C is an illustration of a third conjugate according to the present invention;

FIG. 12 is table of experimental samples used;

DETAILED DESCRIPTION OF THE PREFERRED EMBODIMENTS

Figure 2A:
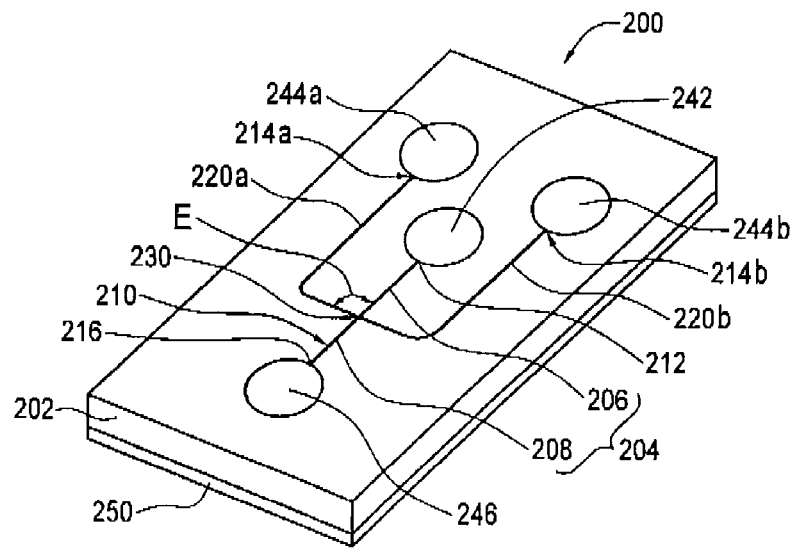
FIG. 2A is a perspective view of a microfluidic chip according to the present invention.

Referring now to FIGS. 1A through 4G, there is shown a test system 100 according to a preferred embodiment of the present invention. The test system 100 is for use with a buffer 50 to test for the presence of target molecules 46a, 46b, 46c (46a-c) of one or more target types in a biological test sample 40. The test system 100 preferably includes a first set of test molecules 102, a microfluidic chip 200, an irradiating device 300, and a detection device 400. The test system 100 also preferably includes a housing 500 encasing the irradiating device 300 and the detection device 400, with housing 500 being sized and adapted for portable, hand-held, and point-of-care diagnostic use.

Introduction to the System

Preferably, the first set of test molecules 102 may include (i) detection molecules 106a, 106b, 106c (106a-c) and (ii) conjugates 126a, 126b, 126c of the detection molecules 106a-c and the target molecules 46a-c, if present in the test sample 40.

As best seen in FIGS. 1A through 1C, the detection molecules 106a-c are of one or more detection molecule types. Each of the detection molecule types is conjugable with a respective one of the target types. Each of the detection molecules 106a-c preferably includes a microbead 108 along with one or more—and preferably a plurality of—bio-recognition molecules 116 (BRMs 116) bound to the surface of the microbead 108 by a carboxylic acid 118. Each of the BRMs 116 is specific for one of the target types of the target molecules 46a-c. Each microbead 108 is preferably bound to a plurality of BRMs 116. The plurality of BRMs 116 bound to the microbead 108 may collectively be conjugable with more than one—but, preferably, are collectively conjugable with only a single one—of the target types. Each microbead 108 is preferably also tagged with one or more BRM fluorophores 112a-b that are coupled to the microbead 108. The BRM fluorophores 112a-b preferably include one or more quantum dots 112a, 112b of one or more quantum dot types. In some cases, and as best seen in FIG. 1C, the quantum dots 112a, 112b may be of two or more quantum dot types—e.g., red quantum dots 112b and yellow quantum dots 112a. Alternately, the BRM fluorophores 112a-b may include one or more fluorescent dyes (not shown) of one or more fluorescent dye types.

As best seen in FIGS. 1A through 1C, the conjugates 126a, 126b, 126c are of one or more conjugate types each corresponding to a different one of the detection molecule types in conjugation with its corresponding target type. The conjugates 126a, 126b, 126c are preferably less than about 10 micrometers (μm) in size. In some embodiments, the conjugates 126a, 126b, 126c may be less than about 5 μm in size, or even less than about 1 μm in size. Preferably, and as best seen in FIGS. 1A through 1C, each of the conjugates 126a, 126b, 126c also includes a target marker fluorophore 130 bound to a respective one of the target molecules 46a, 46b, 46c.

Figure 2B:
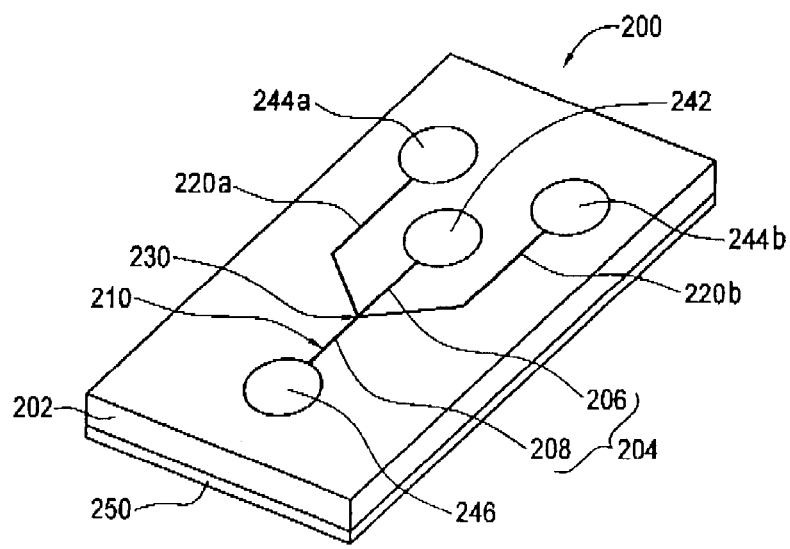
FIG. 2B is a perspective view of an alternate microfluidic chip according to the present invention.

As best seen in FIGS. 2A and 2B, the microfluidic chip 200 preferably includes a chip substrate portion 202 and a glass slide 250 underlying the chip substrate portion 202. The chip substrate portion 202 is preferably fabricated from polydimethylsiloxane (PDMS), which is shaped to define one or more elongate sample channels 204, and one or more flow focusing channels 220a, 220b, therein. The flow focusing channels 220a, 220b are in fluid communication with at least one of the sample channels 204. Preferably, the chip substrate portion 202 is additionally shaped to define a sample well 242, two buffer wells 244a, 244b, and a terminal well 246 therein.

Figure 2C:
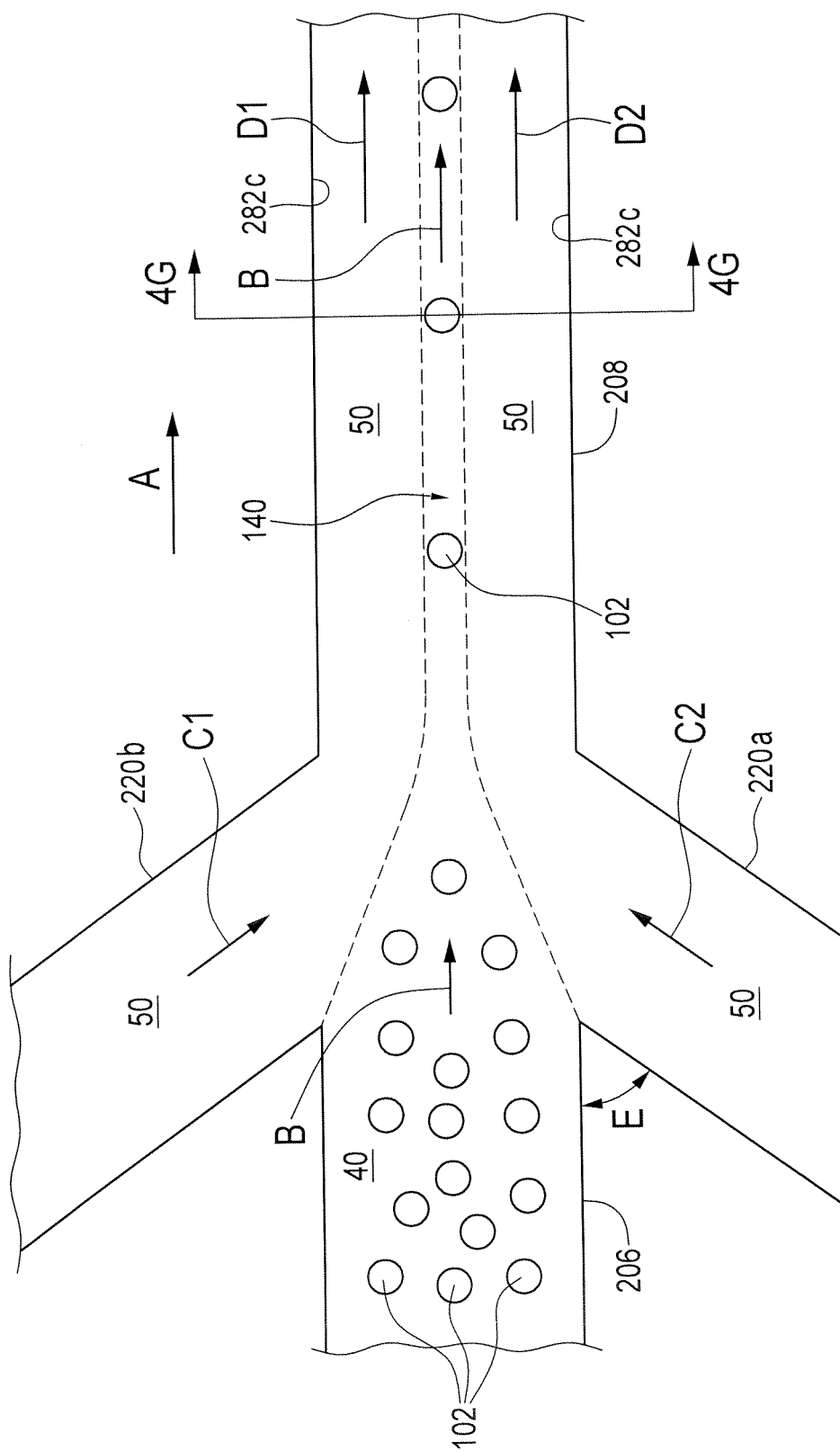
FIG. 2C is a close-up top view of the microfluidic chip intersection of FIG. 2B.
Figure 4A:
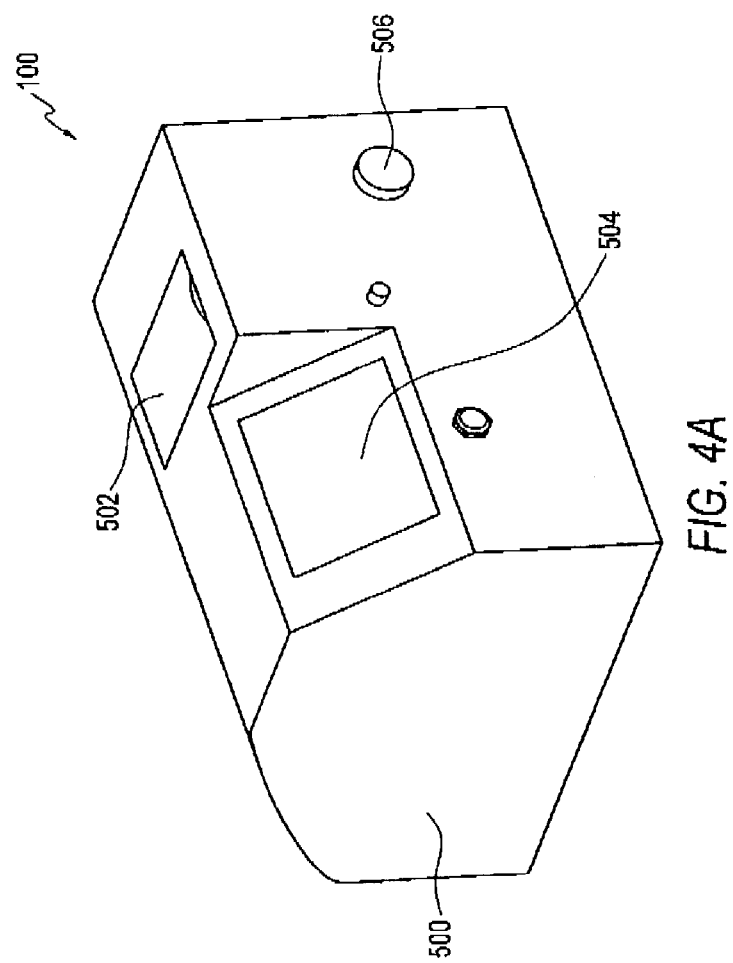
FIG. 4A is a perspective view of the system housing.
Figure 4B:
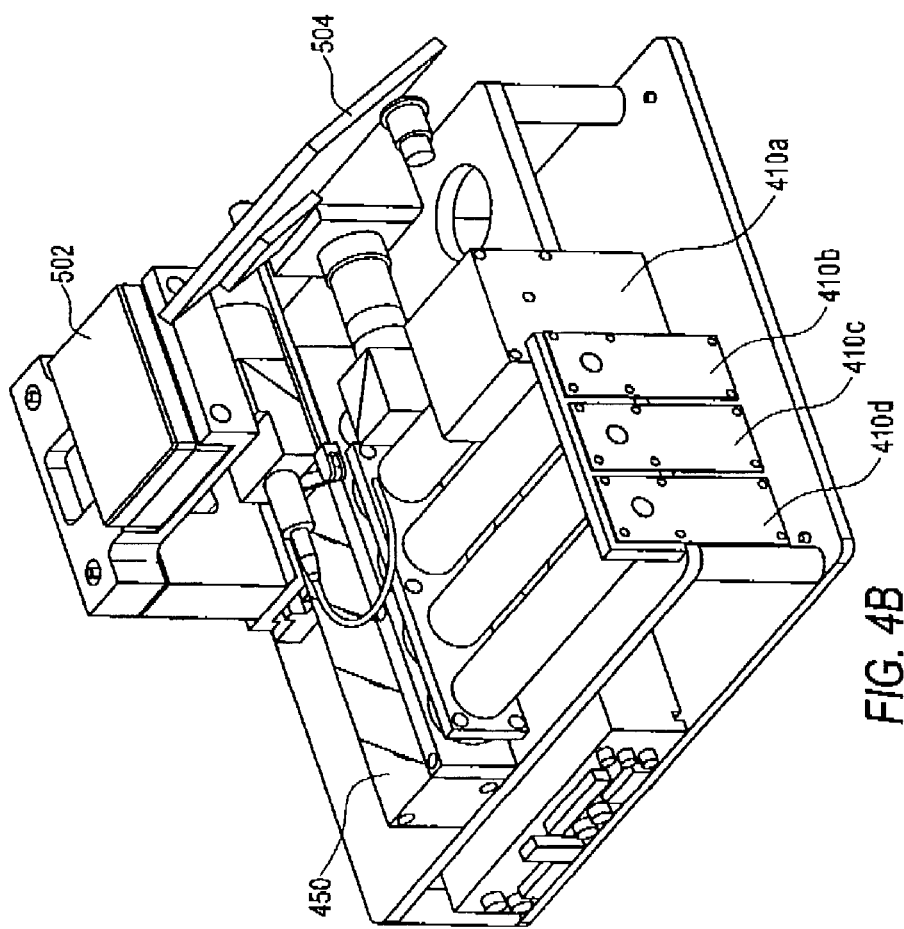
FIG. 4B is a perspective view of the system with the housing removed.
Figure 4C:
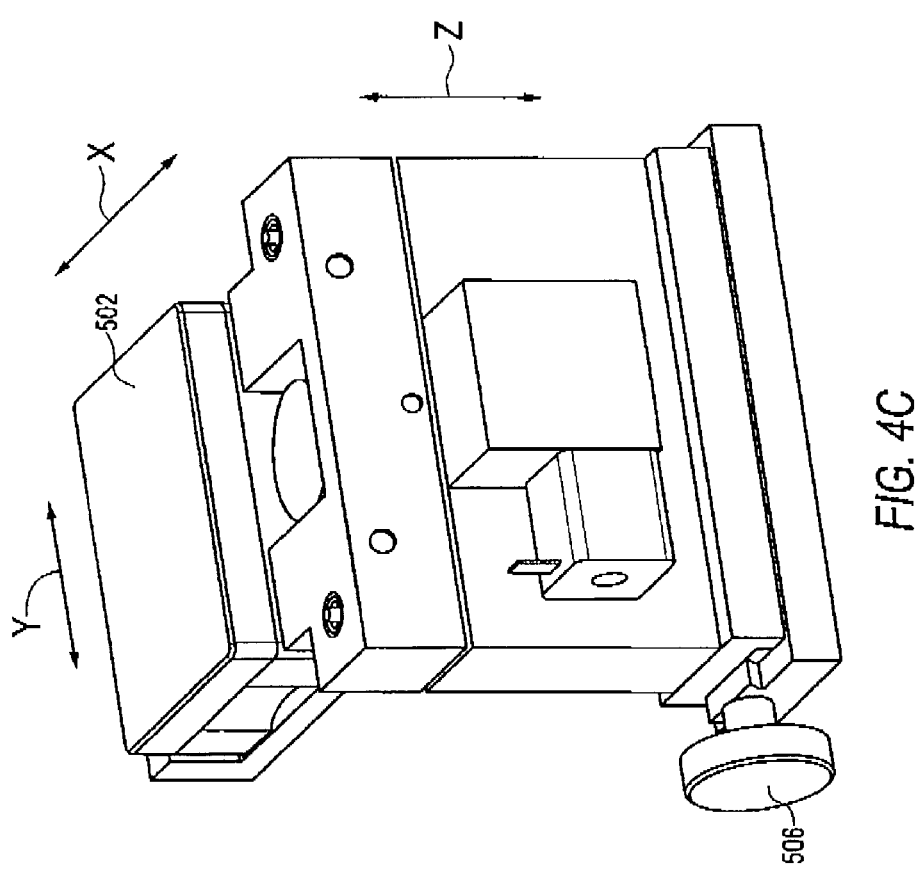
FIG. 4C is a perspective view of the microchip platform and irradiation device with the sample hatch closed.
Figure 4D:
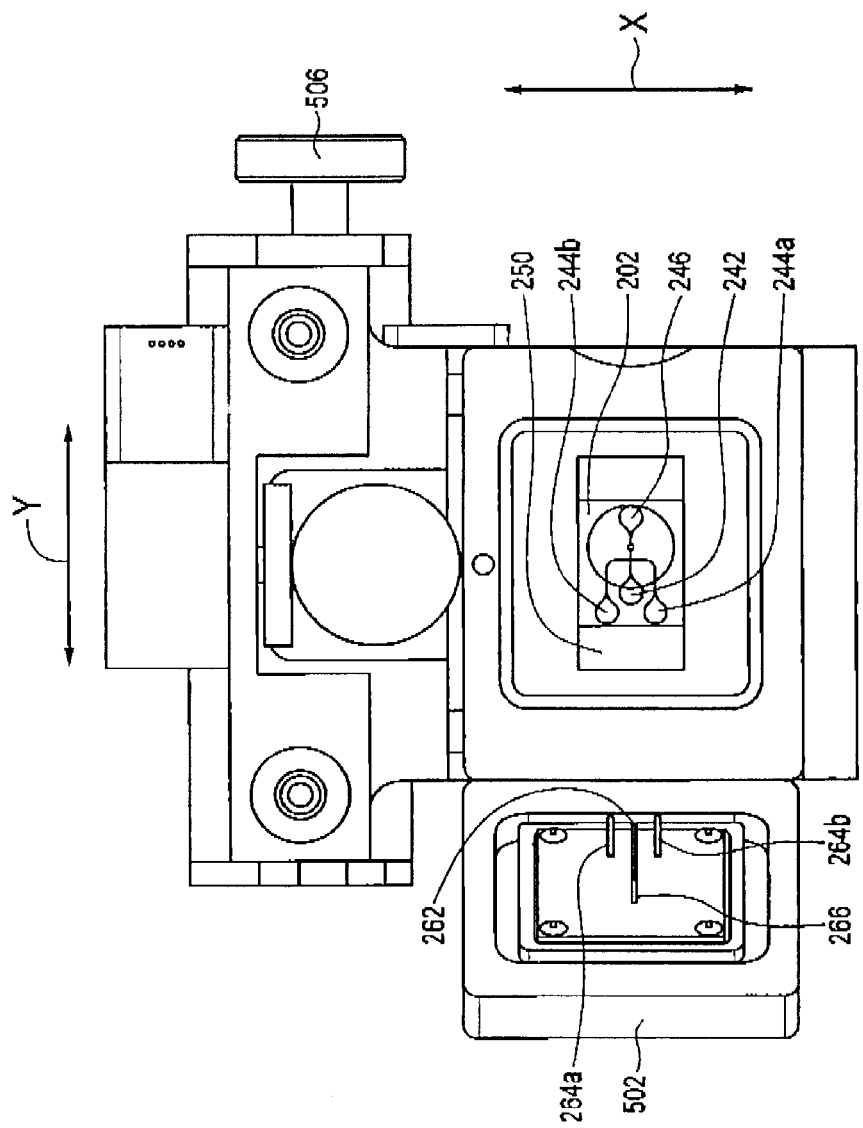
FIG. 4D is a top view of the microchip platform with the sample hatch open.
Figure 4E:
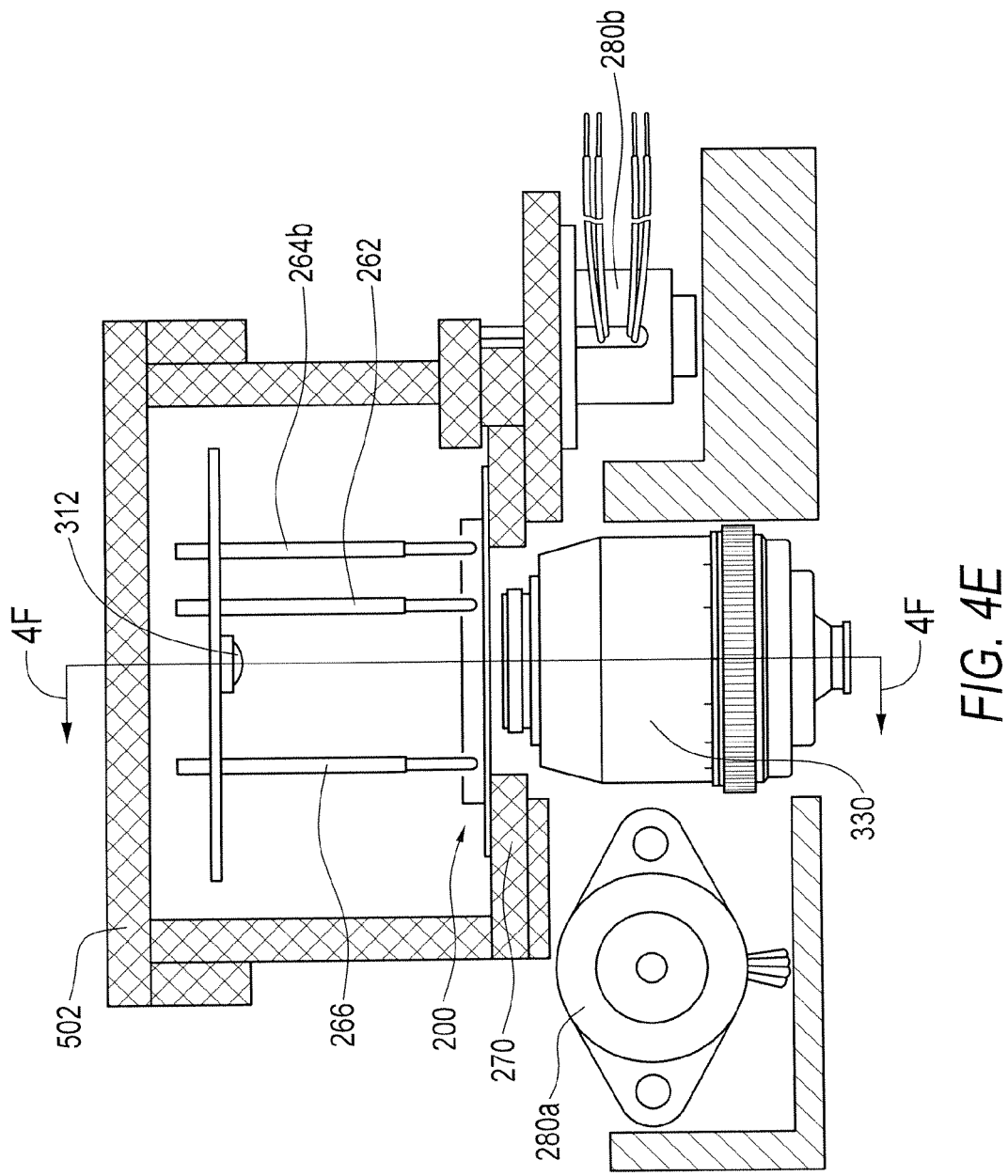
FIG. 4E is a side view of the lens, motors and microchip platform.
Figure 4F:
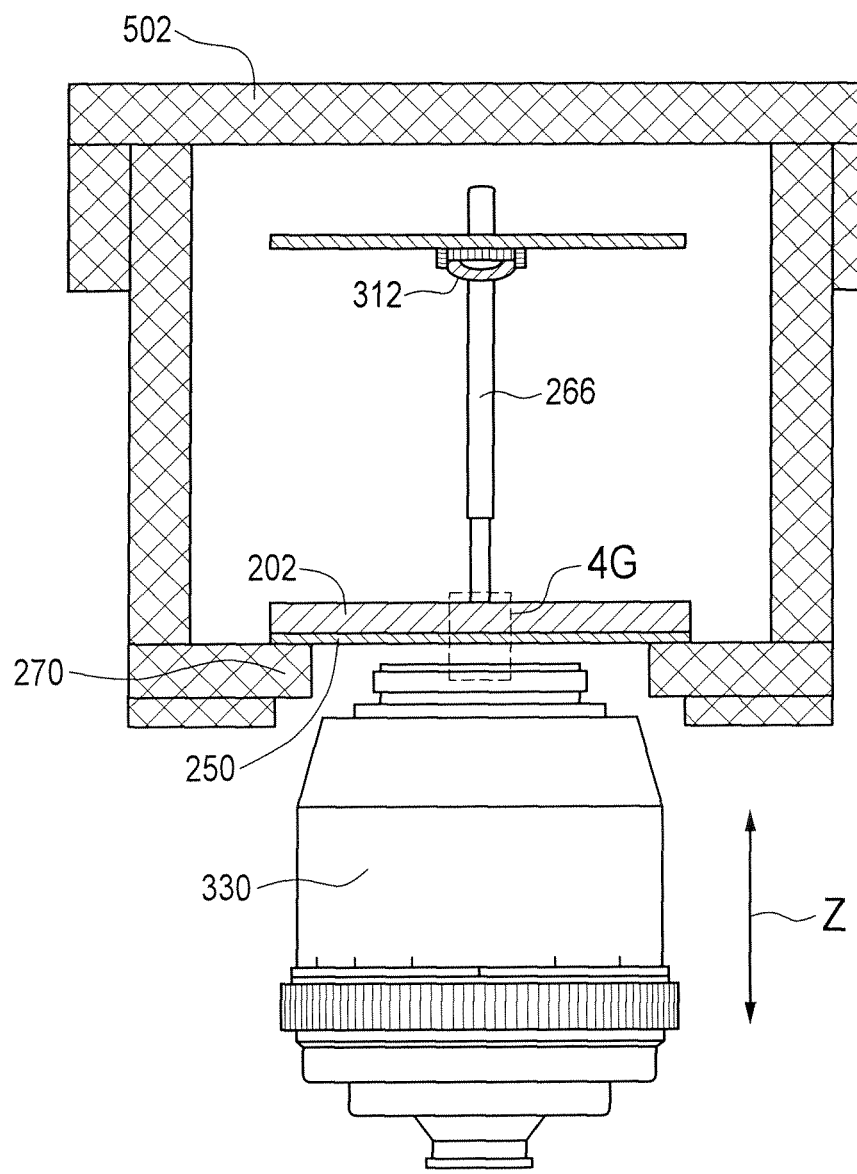
FIG. 4F is a cross-section schematic of the lens and microfluidic chip platform along line 4F-4F of FIG. 4E.
Figure 4G:
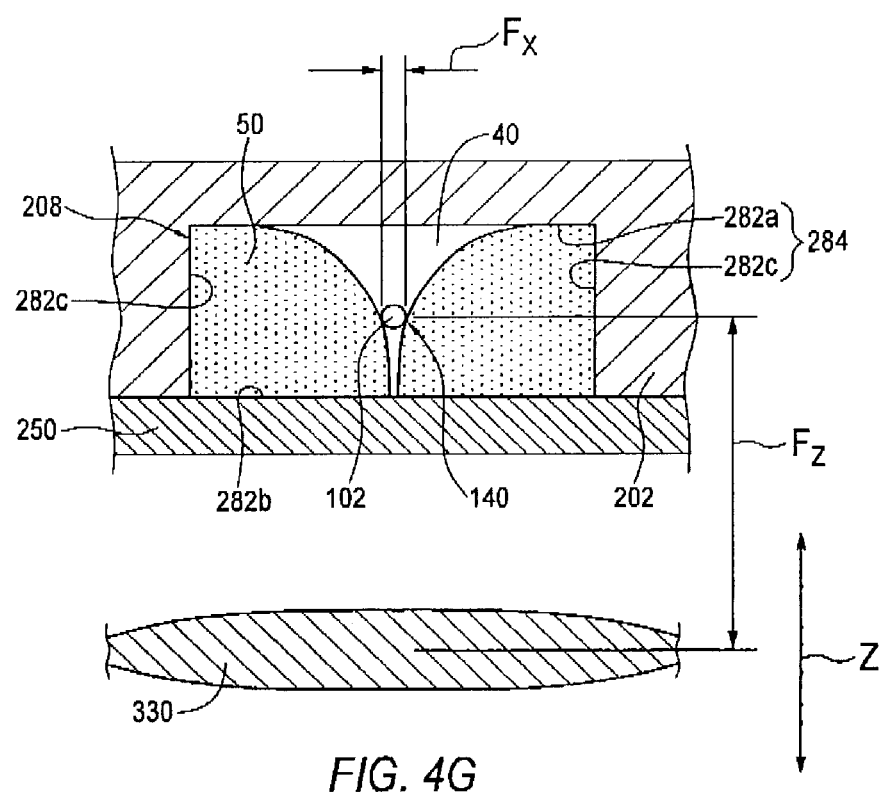
FIG. 4G is a close-up schematic of the indicated section of FIG. 4F and a cross-section along line 4G-4G of FIG. 2C.

As best seen in FIG. 2C, the sample channels 204 are sized to enable passage therethrough of the test molecules 102. As best seen in FIGS. 2A to 2C, the sample channels 204 include a sample supply channel 206, and a sample focused channel 208 in fluid communication with the sample supply channel 206. The sample well 242 is adjacent to a sample starting point 212 of the sample supply channel 206—i.e., upstream (i.e., in a direction generally opposed to arrow "A") of the flow focusing channels 220a, 220b. The sample focused channel 208 is downstream (in the direction indicated generally by arrow "A") of the flow focusing channels 220a, 220b. The terminal well 246 is adjacent to an end point 216 of the sample focused channel 208—i.e., downstream (in the direction indicated generally by arrow "A") of the flow focusing channels 220a, 220b. As best seen in FIG. 4G, the sample focused channel 208 is defined by one or more elongate channel walls 284 of the chip substrate portion 202. The channel walls 284 include a top channel portion 282a and two opposing side channel portions 282c. As best seen in FIG. 4G, the glass slide 250 defines a bottom channel portion 282b of the sample focused channel 208.

The flow focusing channels 220a, 220b are for operative passage therethrough of the buffer 50. As best seen in FIG. 2C, there are preferably two flow focusing channels 220a, 220b, which adjoin the sample channels 204 upstream (i.e., in a direction generally opposed to arrow "A"), and from opposing sides 282c,282c, of the sample focused channel 208. As shown in FIG. 2A, each buffer well 244a, 244b is adjacent to a buffer starting point 214a, 214b of a respective one of the flow focusing channels 220a, 220b. Each of the flow focusing channels 220a, 220b may adjoin the sample channels 204 at an adjoining angle (as indicated generally by arrow "E" in FIGS. 2A and 2C) of about 90 degrees (as shown in FIG. 2A), about 45 degrees (as best seen in FIG. 2C), or another potentially advantageous adjoining angle "E". As shown in FIGS. 2A and 2B, the two flow focusing channels 220a, 220b preferably adjoin the sample channels 204 at a common intersection portion 230.

As shown in FIG. 2C, the buffer 50 exits from the flow focusing channels 220a, 220b and operatively directs a single-file stream 140 of the test molecules 102 through at least one of the sample channels (i.e., the sample focused channel 208)—preferably by less than about 10 micrometers (μm) downstream "A" of the common intersection portion 230. The buffer 50 also operatively flows through the sample focused channel 208. As indicated generally by the relative lengths of arrows "B", "D1" and "D2" in FIG. 2C, a buffer flow rate (as indicated generally by arrows "D1", "D2") of the buffer 50 is typically higher than a test flow rate (as indicated generally by arrow "B") of the test molecules 102 in the single-file stream 140. The single-file stream 140 is directed along a sample path (as indicated generally by arrow "B") that is preferably in spaced relation from the opposing side channel portions 282c,282c (as best seen in FIG. 2C), and from the bottom channel portion 282b and the top channel portion 282a (as best seen in FIG. 4G).

Passage of the test molecules 102 through the sample focused channel 208 is preferably facilitated by electrokinetic flow. Accordingly, and as best seen in FIG. 4D, the test system 100 preferably also includes a sample well electrode 262, two buffer well electrodes 264a, 264b, and a terminal well electrode 266. The positioning of the electrodes 262, 264a, 264b and 266 may be best appreciated from a consideration of FIGS. 4D and 4E. The sample well electrode 262 is operatively positioned in the sample well 242. Each buffer well electrode 264a, 264b is operatively positioned in one of the buffer wells 244a, 244b. The terminal well electrode 266 is operatively positioned in the terminal well 246.

The sample well electrode 262 is operatively supplied with a first electrical potential of a first polarity. The terminal well electrode 266 is operatively supplied with a second electrical potential of an opposing second polarity. Each buffer well electrode 264a, 264b is operatively supplied with a third electrical potential of the first polarity. Preferably, the third electrical potential is higher than the first electrical potential, with a ratio of the third electrical potential relative to the first electrical potential being about 1.8:1 (9:5).

Preferably, the test flow rate "B" of the test molecules 102 in the single-file stream 140 is at least about thirty (30) test molecules 102 per minute. More preferably, the test flow rate "B" may be at least about sixty (60) test molecules 102 per minute. Preferably, even higher test flow rate "B"s—e.g., about five hundred (500) test molecules 102 per minute—may afford even more advantageous utility.

Figure 3A:
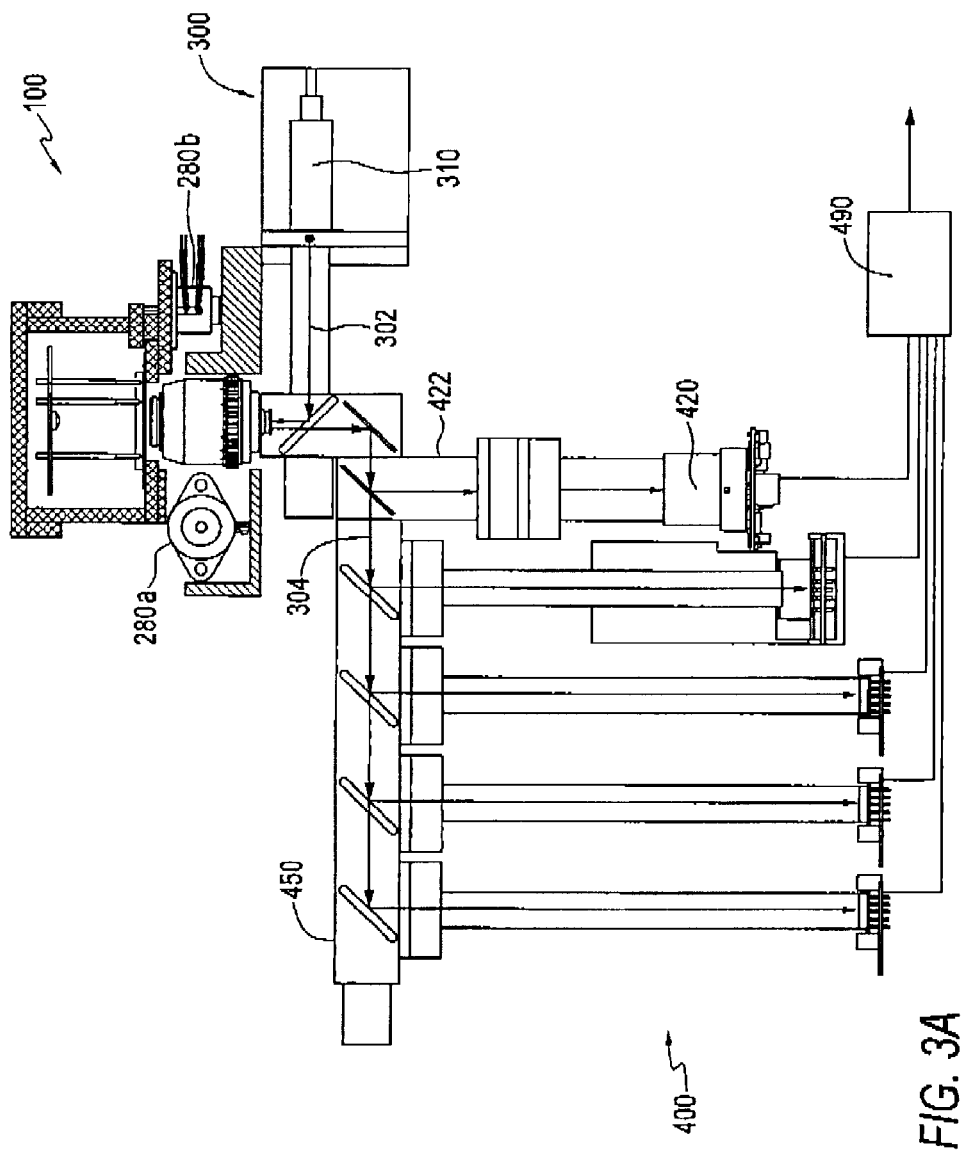
FIG. 3A is a schematic of a test system according of the present invention.
Figure 3B:
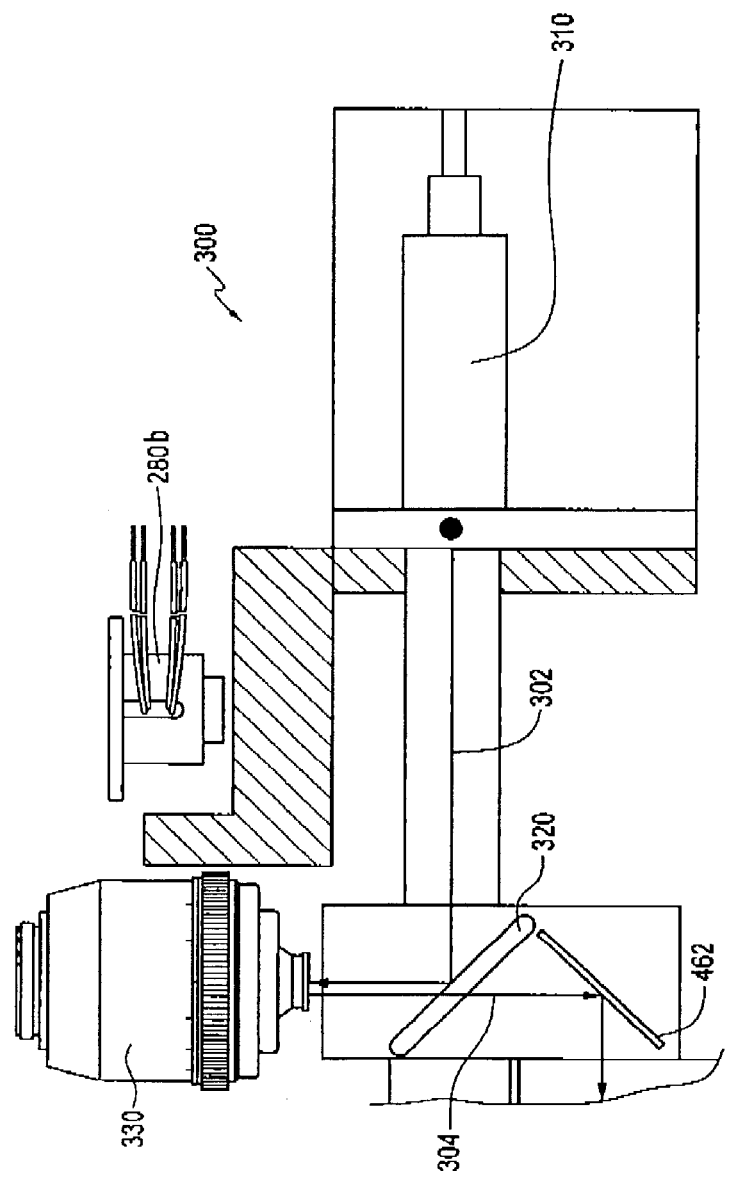
FIG. 3B is a schematic of the irradiation device of FIG. 3A.

As best seen in FIGS. 3A and 3B, the irradiating device 300 operatively delivers electromagnetic frequency (EMF) radiation 302, at an irradiation position 210 (best seen in FIGS. 2A and 23) along the sample focused channel 208, for absorption by the test molecules 102 in the single-file stream 140. The irradiating device 300 may include an LED 312 (as best seen in FIGS. 4E and 4F) and/or a laser 310 (as best seen in FIGS. 3A and 3B) to operatively emit the EMF radiation 302. Preferably, the laser 310 has an operating power of between about 2 milliwatts (mW) and about 50 mW, and more preferably, between about 20 mW and about 25 mW. Preferably, the EMF radiation 302 may have an EMF wavelength of about 488 nm.

Figure 3C:
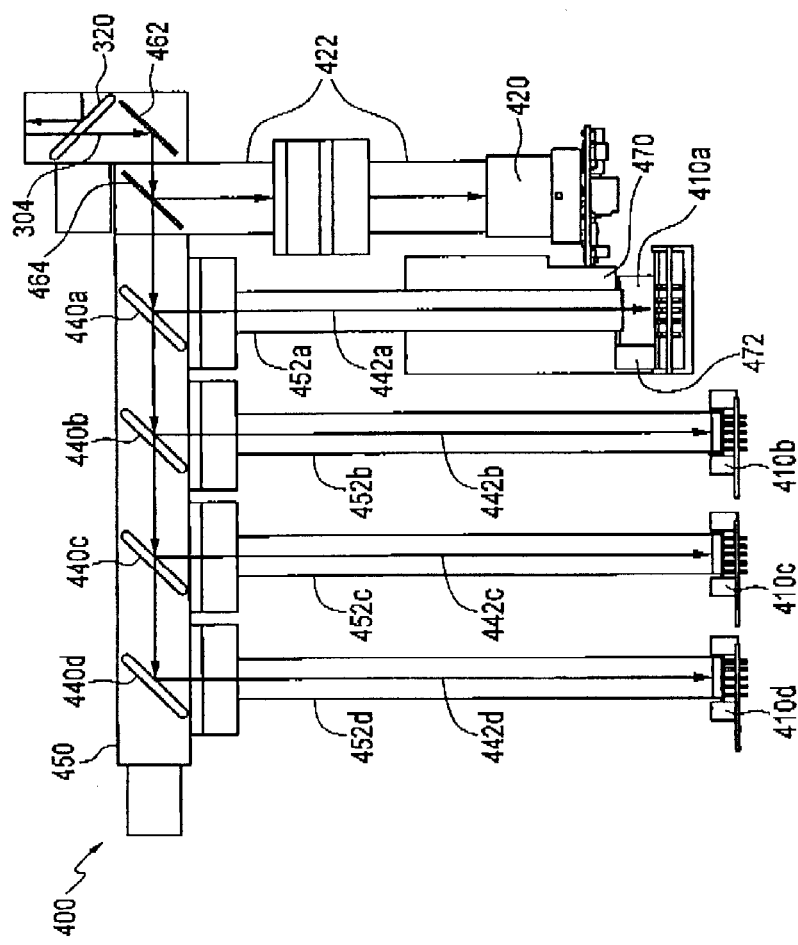
FIG. 3C is a schematic of the detection device of FIG. 3A.

As best seen in FIGS. 3A to 3C, the test molecules 102 emit fluorescence 304 after absorption of the EMF radiation 302. The fluorescence 304 of the test molecules 102 includes a distinct fluorescent spectrum 726a, 726b, 726c (as best seen in FIGS. 7A to 7C) for each one of the conjugate types. Preferably, and as best seen in FIGS. 6A to 7C, after absorption of the EMF radiation 302, the BRM fluorophores 112a-b—whether quantum dots 112a, 112b or fluorescent dyes (not shown)—emit at least a BRM part 604a, 604b, 604c, and the target marker fluorophore 130 emits a target part 604d, of the fluorescence 304 of the distinct fluorescent spectrum 726a, 726b, 726c after absorption of the EMF radiation 302. (The target part 604d may have a lower intensity than the BRM part 604a, 604b, 604c, of the fluorescence 304 of the distinct fluorescent spectrum 726a, 726b, 726c for each of the conjugates 126a, 126b, 126c.) The BRM fluorophores 112a, 112b and the target marker fluorophore 130 together emit the fluorescence 304 of the distinct fluorescent spectrum 726a, 726b, 726c after absorption of the EMF radiation 302.

Though not shown in the figures, the test system 100 may alternately include a fiber optic cable delivering the fluorescence 304 to the detection device 400 from substantially adjacent to the irradiation position 210 (i.e., along the sample focused channel 208).

As may be best appreciated from a consideration of FIGS. 3A, 3C, 6A and 7A-9, the detection device 400 monitors the single-file stream 140 for the fluorescence 304 emitted by the test molecules 102. Generally speaking, the detection device 400 identifies the presence of the conjugates 126a, 126b, 126c in the first set of test molecules 102 by monitoring for the distinct fluorescent spectrum 726a, 726b, 726c (as best seen in FIGS. 7A to 7C) of each one of the conjugate types.

As best seen in FIG. 3C, the detection device 400 may preferably include avalanche photodetectors 410a, 410b, 410c, 410d (APDs 410a-d), a charge-coupled device 420, and/or one or more trip sensors (not shown), so as to monitor the single-file stream 140 for the fluorescence 304 emitted by the test molecules 102. Preferably, the detection device 400 includes two, three, four, or more APDs 410a-d monitoring the single-file stream 140 for the fluorescence 304 emitted by the test molecules 102. Each of the APDs 410a-d is preferably adapted to receive and identify the presence of a different range of wavelengths—e.g., blue (not shown), green 602d, yellow 602a, orange 602c, or red 602b ranges of wavelengths.

In some embodiments of the invention, a first one of the APDs 410a-d may preferably be adapted to receive and identify the presence of the BRM part 604a, 604b, 604c, with a second one of the APDs 410a-d being adapted to receive and identify the presence of the target part 604d, of the fluorescence 304 of the distinct fluorescent spectrum 726a, 726b, 726c for each of the conjugates 126a, 126b, 126c. In such embodiments, the second one of the APDs 410a-d may preferably have a greater sensitivity than the first one of the APDs 410*a-d*. Where the detection device 400 additionally includes a charge-coupled device 420, it may also include a switch means 464 (as best seen in FIG. 3C) for switching between monitoring the single-file stream 140 with either the APDs 410*a-d* or the charge-coupled device 420.

Figure 9:
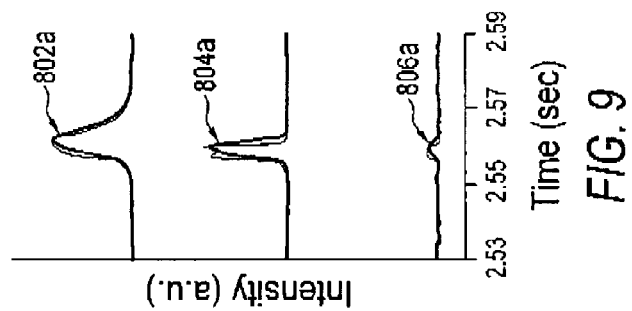
FIG. 9 is a close-up of the indicated section of FIG. 8A
Figure 8A:
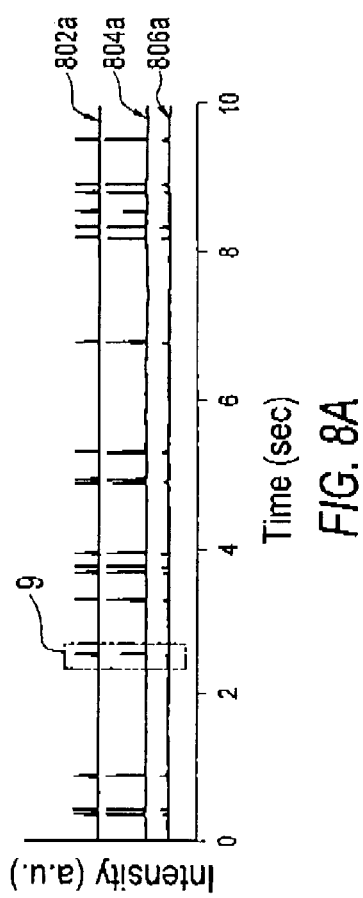
FIG. 8A is a graph of intensity vs. time measurements for the BRM conjugates of FIG. 1A.

As aforesaid, and though not shown in the figures, the detection device 400 may include a series of one or more trip sensors. Each such trip sensor may preferably generate a digital signal corresponding to an intensity 802*a*, 802*b*, 802*c* (as best seen in FIGS. 8A-9) of the fluorescence 304, but only when the intensity of the fluorescence 304 is in excess of a minimum trip intensity. Each trip sensor in the series may preferably be provided with a different pre-determined minimum trip intensity. The series of trip sensors may preferably be arranged in ascending or descending order of minimum trip intensities.

In this manner, the test system 100 identifies the presence of the target molecules 46*a*, 46*b*, 46*c* in the test sample 40. Preferably, the test system 100 is particularly suited for use with blood, urine, sputum, and serum test samples. It is intended to be used for diagnosis of infectious diseases, and/or of bacterial disease states, viral disease states, fungal disease states, and/or vector-induced disease states. In particular, the test system 100 may be particularly useful in simultaneously diagnosing whether an organism is infected with HIV, HBV or HCV.

At this stage, it may be worthwhile to specifically note that, in some embodiments falling within the scope of the invention, the test system 100 may be provided without (though preferably still for use with) one or more of its aforementioned component parts. That is, and for example, the test system 100 may be provided without the test molecules 102, though it might still be intended for use with same. Similarly, the test system 100 may be provided without one or more of the microfluidic chip 200, the irradiating device 300, and the detection device 400—though, of course, it might still be intended for use with same. For example, where the test system 100 is provided with neither the irradiating device 300 nor the detection device 400, it may be intended for use with a combined irradiating and detection device 300, 400.

Introduction to the Method

In accordance with the present invention there also disclosed a method, inter alia, of focusing molecules to facilitate a test for the presence of target molecules 46*a*, 46*b*, 46*c* of one or more target types in a biological test sample 40. The method preferably includes:

a detection molecule forming step,
a conjugate-forming step after the detection molecule forming step,
an electrokinetic step,
a sample flowing step after the conjugate-forming step,
a buffer flowing step,
a sample focusing step after the electrokinetic step and the buffer flowing step,
an irradiating step after the sample focusing step,
a fluorescence-detecting step after the irradiating step, and/or
a conjugate-identifying step after the irradiating step.

In the detection molecule forming step, a microbead 108 is tagged with one or more BRM fluorophores 112*a*, 112*b* that are coupled to the microbead 108. In the conjugate-forming step, the conjugates 126*a-c* are preferably formed by introducing target marker fluorophores 130 and detection molecules 106*a-c* (of one or more detection molecule types) into the biological test sample. Each of the detection molecule types is conjugable with a respective one of the target types, and the target marker fluorophores 130 is preferably conjugable/bindable with one or more (and/or all) of the target types. As such, if the target molecules 46*a*, 46*b*, 46*c* are present in the test sample, the test molecules 102 may preferably include conjugates 126*a*, 126*b*, 126*c* of the detection molecules 106*a-c*, the target marker fluorophores 130, and the target molecules 46*a*, 46*b*, 46*c*. Preferably, the conjugates 126*a*, 126*b*, 126*c* formed in the conjugate-forming step are less than about 10 micrometers (μm) in size. In some embodiments, the conjugates 126*a*, 126*b*, 126*c* formed may be less than about 5 μm in size, or even less than about 1 μm in size. The conjugates 126*a*, 126*b*, 126*c* so formed are of one or more conjugate types, each corresponding to a different one of the detection molecule types in conjugation with the corresponding target type.

In the electrokinetic step: (i) a first electrical potential of a first polarity is supplied to the sample supply channel 206, i.e., upstream (i.e., in a direction generally opposed to arrow "A") of the flow focusing channels 220*a*, 220*b*; (ii) a second electrical potential of an opposing second polarity is supplied to the sample focused channel 208, i.e., downstream "A" of the flow focusing channels 220*a*, 220*b*; and (iii) a third electrical potential of the first polarity is supplied to each of the flow focusing channels 220*a*, 220*b*. The third electrical potential is preferably higher than the first electrical potential. A ratio of the third electrical potential relative to the first electrical potential is preferably about 1.8:1 (i.e., about 9:5). In the sample flowing step, the test molecules 102 are passed through the sample supply channel 206. In the buffer flowing step, the buffer 50 is passed through the flow focusing channels 220*a*, 220*b*, adjoining the sample channels 204.

In the sample focusing step, a single-file stream 140 of the test molecules 102 is directed through the sample focused channel 208 by passage of the buffer 50 from two flow focusing channels 220*a*, 220*b* into the sample focused channel 208 via an adjoining common intersection portion 230. The single-file stream 140 is directed along a sample path "B" that is in spaced relation from the opposing side channel portions 282*c*,282*c*, from the top channel portion 282*a*, and from the bottom channel portion 282*b* of the sample focused channel 208. Typically, the buffer 50 flows into the sample focused channel 208 at a buffer flow rate "D1", "D2" that is higher than a test flow rate "B" of the test molecules 102 in the single-file stream 140. In the sample focusing step, the buffer 50 may flow into the sampled focused channel from an adjoining angle "E" of about 90 degrees (as shown in FIG. 2A), about 45 degrees (as best seen in FIG. 2C), or from another potentially advantageous adjoining angle "E". Preferably, in the sample focusing step, passage of the single-file stream 140 of the test molecules 102 through the sample focused channel 208 is facilitated by the electrokinetic step.

In the irradiating step, electromagnetic frequency (EMF) radiation 302 is delivered to the test molecules 102 in the single-file stream 140, preferably by a laser 310 having an operating power of between about 2 mW and about 50 mW. More preferably, the operating power may be between about 20 mW and about 25 mW. In one preferred embodiment, the EMF radiation 302 has an EMF wavelength of about 488 nm.

After absorption of the EMF radiation 302, each of the conjugates 126*a*, 126*b*, 126*c* (i.e., of each conjugate type) emits fluorescence 304 of a distinct fluorescent spectrum 726*a*, 726*b*, 726*c*. The target marker fluorophores 130 emit a target part 604*d*, and the BRM fluorophores 112*a*, 112*b* emit a BRM part 604*a*, 604*b*, 604*c*, of the distinct fluorescent spectrum 726*a*, 726*b*, 726*c* for each conjugate type.

In the fluorescence-detecting step, the single-file stream 140 is monitored for fluorescence 304 emitted by the test molecules 102. The fluorescence 304 emitted by the conjugates 126a, 126b, 126c is preferably received by two or more APDs 410a-d—with first and second APDs 410a-d receiving and identifying the BRM part 604a, 604b, 604c and the target part 604d, respectively, of the fluorescence 304 of the distinct fluorescent spectrum 726a, 726b, 726c for each of the conjugates 126a, 126b, 126c. Alternately, the fluorescence 304 emitted by the conjugates 126a, 126b, 126c may be received by a charge-coupled device 420. Still further, in the fluorescence-detecting step, the fluorescence 304 emitted by the conjugates 126a, 126b, 126c may be selectively received by the APDs 410a-d, the charge-coupled device 420, or both.

Finally, in the conjugate-identifying step, the presence of the target molecules 46a, 46b, 46c in the test sample 40 is identified when the distinct fluorescent spectra 726a, 726b, 726c of the conjugate types is detected.

The System in Greater Detail

The test system 100 according to the invention will now be discussed in considerably greater detail.

The test system 100 is designed to test biological test samples (i.e. blood, sputum, serum, urine, etc.) for various conditions and infectious diseases in the host who provided the sample. Infectious diseases tested can include, but are not limited to, bacterial disease states, viral diseases states, fungal disease states, vector-induced diseases states, and combinations thereof. Testing is performed by combining detection molecules 106a-c with the biological sample to form a test sample 40.

The test molecules 102 may preferably include conjugates 126a-c as illustrated in FIGS. 1A, 1B and 1C. Each of the conjugates 126a-c preferably includes a detection molecule 106a-c. The detection molecule 106a-c preferably includes a polymer microbead 108, with embedded BRM fluorophores, such as quantum dots 112a-b creating a unique spectral pattern or "barcode" associated with each detection molecule 106a-c. The detection molecule 106a-c preferably further includes a BRM 116 bound to the surface of the microbead 108 by a carboxylic acid 118. The target molecule 46a-c with its target marker fluorophore 130 is thus bound to the exterior of the microbead 108 through BRM 116 to form the conjugate 126a-c.

Figure 5A:
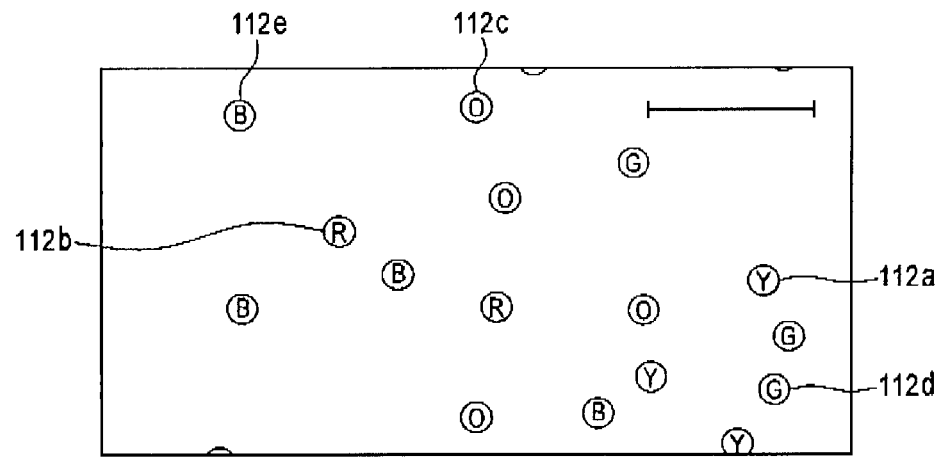
FIG. 5A is an illustration of fluorescing quantum dots.
Figure 5B:
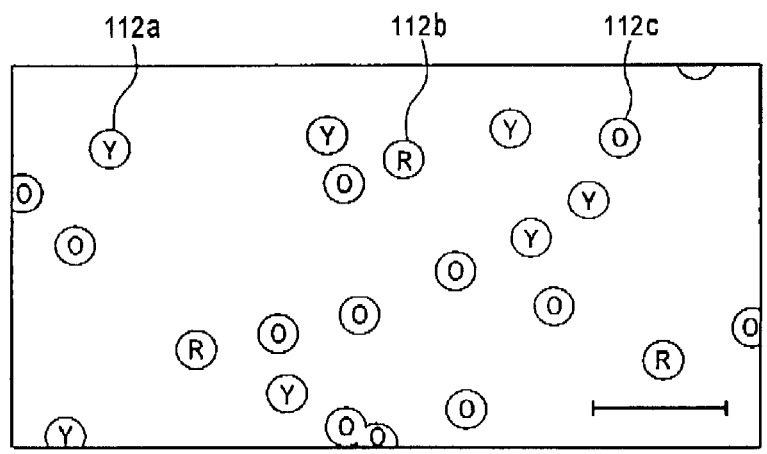
FIG. 5B is an illustration of fluorescing quantum dots.

More specifically, with reference to FIG. 1A, the microbead 108 has embedded BRM fluorophores shown as yellow quantum dots 112a. FIGS. 1B and 1C show other various combinations of red (112b), and red (112b) and yellow (112a). As also shown for reference in FIGS. 5A and 5B, orange (112c), green (112d) and blue (112e) quantum dots can also be used. Alternative fluorophores, such as fluorescent dyes, can be used in place of quantum dots. Each BRM fluorophore produces a distinct fluorescent spectrum, such as shown in FIG. 6A—e.g., distinct fluorescent spectrum 604b for red quantum dots. The target type 46a is conjugated to detection molecule 106a to form, together with the target marker fluorophore 130, the conjugate 126a. Similarly, in FIGS. 1B and 1C, target types 46b and 46c are conjugated to detection molecules 106b and 106c to form, together with the target marker fluorophores 130, conjugates 126b and 126c, respectively.

Assembly

FIG. 3A shows a schematic of an embodiment the present inventive system 100. The test system 100 is generally comprised of a microfluidic chip 200, and irradiating device 300 and a detection device 400.

The microfluidic chip 200, as best shown in FIGS. 2A and 2B, comprises a chip substrate portion 202 mounted on a glass slide 250. The chip substrate is comprised of a number of wells and connecting channels. As shown in FIG. 2B, the exemplary chip 200 has four wells: a sample well 242, two buffer wells 244a and 244b, and a terminal well 246. The sample well 242 is connected at sample starting point 212 to a sample channel 204, which has two parts, a sample supply channel 206 and a sample focused channel 208. Similarly, the buffer wells 244a and 244b are respectively connected at buffer starting points 214a and 214b to flow focusing channels 220a and 220b. The sample supply channel 206 joins the flow focusing channels 220b and 220b at a common intersection 230, with the resulting focused buffer/sample flow entering sample focused channel 208 and terminating at end point 216 into terminal well 246. Along sample focused channel 208 is an irradiating position 210 for aiming the irradiating device 300.

Two variants of the flow focusing channels 220a and 220b are shown in FIGS. 2A and 2B respectively. In FIG. 2A, the flow focusing channels 220a and 220b enter the intersection 230 at substantially a 90-degree angle to the sample supply channel 206 and sample focused channel 208. In FIG. 2B, the flow focusing channels 220a and 220b enter the intersection 230 at substantially a 45-degree angle to the sample supply channel 206. The geometry of the channels 204 and the angle at the intersection 230 is preferably between a 30-degree and a 90-degree angle of intersection, however, the exact angle is best determined by empirical measurement based on the characteristics of the test sample 40 and buffer 50, as well as the desired flow rate.

Based on FIG. 2B, FIG. 2C provides a close-up cross-sectional schematic of the intersection 230 and the flow patterns of the sample 40 and buffer 50. The general direction of flow towards the terminal well 246 is indicated by arrow A, representing a downstream direction. Sample flow along sample supply channel 206 is indicated by arrow B, representing a sample path. The buffer flow along flow focusing channels 220a and 220b is indicated by arrows C2 and C1, respectively. Buffer flow in the sample focused channel 208 is indicated by arrows D2 and D1. The angle of incidence between the flow focusing channels 220a and 220b and the sample supply channel 206 is shown as E.

As the buffer 50 exits the flow focusing channels 220a and 220b into the intersection, the force of the flowing buffer 50 causes the flowing sample 40 from the sample supply channel 206 to narrow and force the test molecules 102 into a single file stream 140. FIG. 4G shows a cross-section of sample focused channel 208, illustrating that the flow focusing effect of buffer 50 on sample 40 function in the both directions, subject to constraint by the channel walls 284. Note that sample 40 extends to the bottom channel portion 282b defined by the glass slide 250, but narrowly, to prevent adhesion of the test molecules 102 to the bottom channel portion 282b. The buffer 50 covers opposing side channel portions 282c, while both the buffer 50 and sample 40 cover the top channel portion 282a.

The microfluidic chip 200 is mounted on a platform 270 as best shown in detail in FIGS. 4E and 4F. The electrokinetic driving force for the sample 40 and buffer 50 is provided by electrodes that are inserted into each of the wells. Thus, for the chip 200 shown, there are a sample well electrode 262, two buffer well electrodes 264a and 264b, and a terminal well electrode 266. A voltage differential is applied via the electrodes to produce the electrokinetic driving force which carries the sample 40 and buffer 50 along their respective channels.

The microfluidic chip 200 is manufactured according to known methods. One such method uses a polydimethylsiloxane (PDMS) microfluidic chip. The PDMS microfluidic chips are preferably fabricated using conventional soft lithography microfabrication techniques. Photomasks of the desired microchannel pattern are prepared and printed on a transparency. A master is fabricated on Si wafers coated with a layer of photoresist and prebaked. Each wafer then has the photomask laid on top of the photoresist, ink surface down, and is exposed to UV light for a brief duration. Following standard postbaking procedures, the wafers are immersed in nanodeveloper to dissolve away any photoresist not exposed to the UV light. The masters are then washed with isopropanol and dried with compressed $N_2$ gas.

The polydimethylsiloxane (PDMS) is generally supplied as prepolymer kits in two parts; part A is the prepolymer and part B contains a cross-linker. The masters are placed in pyrex Petri dishes and mixed prepolymer was poured on top of each. The samples are then placed under vacuum to degas (remove bubbles from) the prepolymer. An incubation period follows in an oven. Once removed from the oven, the cured PDMS slabs are peeled off the masters and excess polymer around the outside of the microchannel pattern is removed. A single master holds patterns for two polymer microchannels. The surfaces of the PDMS substrates and glass coverslips is then cleaned using scotch tape.

Plasma oxygen pretreatment of the PDMS channels can then be used to make the walls hydrophilic. Both the PDMS substrates 202 and glass slides 250 are loaded into the chamber of a plasma cleaner and exposed to oxygen plasma. Immediately after, the surfaces of the PDMS 202 and slides 250 are brought into contact to irreversibly seal the two substrates together. Double distilled water is dispensed into the microchannels 204 to keep the channel surfaces hydrophilic. Finally, small pieces of glass are placed on top of the channel wells 242, 244a, 244b and 246 to keep the water from evaporating, enabling long term storage of the chips 200.

The irradiating device 300, shown in greater detail in FIG. 3B, emits a stream of EMF (electromagnetic frequency) radiation 302 which is directed onto the irradiating position 210 to irradiate the test molecules 102 flowing in the sample focused channel 208 as discussed above. As shown, laser 310 is used to produce the EMF radiation, however, alternative sources, such as an LED can also be used. The LED can be positioned in the same location as laser 310, or in the position shown by LED 312.

As shown in FIG. 4F, the emitted EMF radiation 302 is directed via a mirror 320 through an objective lens 330 to focus the beam onto the irradiating position 210. The focal length of the lens can be adjusted along the x-, y-, and z-axis (as also shown in FIGS. 4C and 4D) by movement of the chip platform 270 using motors 280a and 280b to align the radiation 302 with the irradiating position 210. Alignment can be performed automatically or manually. Automatic alignment is performed by activating LED 312 and measuring the intensity of the signal, and adjusting the platform in the x- and z-axis for proper alignment with the sample focused channel 208 and irradiating position 210. Alternatively, the y-axis adjustment can be conducted manually to optimize the signal results. Manual alignment is controlled by the user through of adjustment knob 506, the input interface 504, or a combination thereof.

The alignment and focal adjustment of the lens 330 is more clearly shown in FIG. 4G, with the z-axis focal distance, $F_z$, between the lens 330 and the test molecules 102 being adjusted to ensure the test molecules 102 are sufficiently excited by the EMF radiation 302. Similarly, the x-axis focal distance, $F_x$, is adjusted to account for the size (width) of the test molecules 102.

The detection device 400, shown in greater detail in FIG. 3C, generally comprises a collection of mirrors and filters to direct the emitted fluorescence 304 from the irradiated test molecules 102 into fluorescence detection devices. As shown in FIG. 3C, incoming fluorescence 304 is directed along a detection channel 450 by a primary mirror 462. The fluorescence signal is then split by a beam splitter mirror 464. One portion of the split fluorescence signal is directed along an intensity channel 422 to a Charge-Coupled Device ("CCD") 420 which determines the overall intensity of the signal.

The other portion of split fluorescence signal is directed along a detection channel 450 where it passes through a series of bandpass filters 440a-d. Each filter 440a-d covers a specific wavelength corresponding to the fluorescence signals 304 emitted by each of the BRM fluorophores 112a-b and target marker fluorophores 130 in the test molecules 102. The filtered signals 442a-d are each directed along detection channels 452a-d to APDs (Avalanche PhotoDetectors) 410a-d that convert the fluorescence signal into an electrical signal which is then output to a signal processor 490 for analysis.

Taking one signal as an example, a green wavelength bandpass filter 440a is used to divert a filtered portion 442a of the fluorescence signal 304 into detection channel 452a. This filtered signal 442a impacts APD 410a and the result is a green wavelength output signal for analysis. A similar process takes place using yellow bandpass filter 440b, orange bandpass filter 440c and red bandpass filter 440d, with corresponding APDs 410b-d producing output signals for the yellow, orange and red wavelengths. The combined signals collectively produce a spectrum, which is interpreted to determine the identity of the test molecules 102 that have fluoresced.

As the target fluorophore 130 is generally of lower, often substantially lower, intensity than the BRM fluorophores 112a-b, it can be advantageous to have the APD responsible for generating the target fluorophore spectrum to operate at a higher sensitivity than the APDs responsible for generating the BRM conjugate spectra. In the schematic shown, APD 410a is responsible for generating the spectrum of target fluorophore 130, and operates with a greater sensitivity than APDs 410b-d used for the BRM fluorophores 112a-b. As shown, APD 410a is of a type that uses a heat sink 470 to cool the APD, providing greater sensitivity over uncooled APDs 410b-d. Alternately, or in addition to heat sink 470, a temperature control system 472 can be implemented to maintain APD 410a at a constant temperature below ambient.

The overall system is encased in housing 500, which includes sample access port 502 for insertion and removal of sample-loaded microfluidic chips 200, and display 504, which is preferably a touch-screen device to enable dual function as a data-entry device. The housing also includes knobs 506 used to perform manual alignment an adjustment of the position of the chip 200.

Operation

In use, a biological test sample (blood, sputum, serum, urine, etc.) is prepared for insertion into the sample well 242 of the microfluidic chip 200. The biological test sample is combined with a first set of detection molecules to form a test sample 40 which is tested by the system for the presence of target molecules 46 of one or more target types, as determined by the nature of the test. Detection molecules 106 of one or more detection molecule types are individually conjugable with one of the target molecules. Different conjugates of the detection molecules and the target molecules correspond to different detection molecules and target molecules.

A second set of molecules may also be present in the sample, such as unconjugated sample molecules, and the molecules in the second set might travel interspersed in the sample flow with the test molecules (and detection molecules) in the first set. The second set of molecules can be used for multiplexed tests of separate detection molecules, or for system tests such as calibration and error-checking, or ignored as non-relevant.

The microfluidic chip 200 is then inserted into the test system 100 through the sample access port 502 in the housing 500. Alignment of the lens 330 and irradiation position 210 is then performed as discussed above. Operation parameters are input through the display 504 and the necessary electrical potential is applied through electrodes 262, 264a, 264b and 266 to commence flowing of the sample 40 and buffer 50. A first electrical potential is applied to sample well electrode 262, a second electrical potential to buffer well electrodes 264a and 264b, and a third electrical potential to terminal well electrode 266.

The sample 40 and buffer 50 then flow through the sample supply channel 206 and through flow focusing channels 220a and 220b, respectively, as shown in FIG. 2C. The channels 206, 220a and 220b meet at a common intersection 230 and the flow of the sample 40 is focused into a single-file stream 140 of test molecules 102.

The test molecules 102 are then irradiated at an irradiating position 210 by an irradiation device 300. Preferably, an EMF radiation device of a fixed wavelength, such as a laser 310 or LED, is used. The test molecules then emit fluorescence, according to their detection molecule type and/or conjugate type, each having a distinct fluorescent spectrum.

The fluorescence is then detected by a photodetection device, such as an APD or CCD as discussed above, and the resulting signals can be output to a signal processor to identify the conjugate types in the test sample.

Experimental Results

In the example described herein, three pathogens (hepatitis B virus—HBV, hepatitis C virus—HCV, and human immunodeficiency virus—HIV, as illustrated in FIGS. 1A, 1B and 1C, respectively) were selected to demonstrate the utility of this integrated device for infectious disease diagnostics. These three pathogens are all blood-borne viruses, using similar routes of transmission and are among the most prevalent diseases in the world with a significant impact on overall ID morbidity and mortality. For example, HIV infects 40 million, HBV infects 400 million, and HCV infects 170 million people worldwide with an estimated morbidity rate of 39.5 million for HIV, 350 million chronic HBV infections, and 130 million chronic HCV infections. The majority of these cases are located in the developing world. Current diagnostic schemes require three separate tests and relatively large amounts of blood for pathogen detection. These requirements create a significant negative impact on the cost of analysis and speed of analysis. For the developing world, the implementation of a universal diagnostic device has the potential to save many lives.

Quantum Dot Synthesis

CdSe core ZnS capped quantum dots ("Qdots") were synthesized using prior art organometallic methods. Briefly, 12-20 g of tri-noctylphosphineoxide (TOPO, 98% pure, Sigma Aldrich, St. Louis, Mo.) was heated in a three neck flask to 150° C. under Ar gas. 160 µL of dimethylcadmium (97%, Strem Chemicals, Newburyport, Mass.) was injected and mixed in with the heated TOPO for ~15 minutes. After three purges under vacuum, the contents of the three neck flask were heated to 350° C. A 2 molar precursor solution of selenium (Se powder, 99.5%, Sigma Aldrich) and tri-n-octylphosphine (TOP, Sigma Aldrich) was then injected into the three neck and the temperature quickly lowered to 300° C. Cd:Se ratios in the ranges of 1.5:1 to 2.5:1 were used. Qdot emission was tracked during the growth phase by measuring the emission profile of aliquots of the solution in the three neck flask using a fluorimeter (FluoroMax-3, Jobin Yvon Horiba, Edison, N.J.). Once the desired peak emission wavelength had been reached, capping precursor solution consisting of diethyl zinc (Sigma Aldrich), hexamethyldisilathiane (TMS2(S), Sigma Aldrich) and TOP was injected into the three neck drop wise at a rate of ~1 mL/min.

Following Qdot capping, the three neck temperature was lowered to <60° C. and chloroform was added. Several washes with methanol and chloroform (in a 2:1 ratio) were used to precipitate out nanoparticles from unreacted precursors. The final TOPO coated Qdots were stored in chloroform until use.

Quantum Dot Barcode Synthesis

Qdot barcodes or BRM parts (hereinafter "QdotBs") were prepared using known methods (M. Han, X. Gao, J. Z. Su, S. Nie, *Nat. Biotech.*, 19, 631 (2001); X. Gao, S. Nie, *Anal. Chem.*, 76, 2406 (2004)). Briefly, 5 µm diameter polystyrene microbeads (Bangs Laboratories, Fishers, Ind.) with carboxylic acid functional groups on the surface were swollen in propanol and TOPO-coated Qdots in chloroform were added (roughly 1.5×107 beads in 1 mL of propanol and <100 µL of Qdots in chloroform). Owing to hydrophobic-hydrophobic interaction, the Qdots diffused into the microbead interior. The incubation lasted 1 hour for QdotB1 (570 nm emitting Qdots only) and QdotB2 (615 nm emitting Qdots only) samples, while for QdotB3, the incubation was split into two steps with 570 nm emitting Qdots added for the whole hour incubation and 615 nm emitting Qdots added only for the second half hour. The samples were washed several times (between 7-10) with propanol and stored in a fridge at 4° C. until used for an assay. The interval of time between bead preparation and the start of an assay did not exceed 12 hrs.

Antigen Sample Preparation

Pathogen antigens (an exemplary type of the BRMs 116) were then covalently linked to the microbead surface using N-dimethylaminopropyl-N'-ethylcarbodiimide (EDC)-assisted crosslinking. The antigens used were Hepatitis B surface antigen (HBsAg), non-structural protein 4 ($NSP_4$) and glycoprotein 41 (gp41) for HBV, HCV and HIV, respectively.

QdotBs prepared in propanol were vortexed, sonicated for 10 seconds and then run through a 5 mL filter (Falcon, VWR). Samples initially suspended in 1 mL of propanol at a concentration of 1.5×107 beads/mL were split into 250 µL aliquots and centrifuged at 8000 rpm for 3 minutes. The supernatant was aspirated and the QdotBs were resuspended in 100 µL of 0.1 M MES buffer (pH 5.5). Two more washes of the beads with MES buffer were completed and the samples were then resuspended in 90 µL of MES buffer. A stock solution of 0.0092 g N-dimethylaminopropyl-N'-ethylcarbodiimide (EDC, Sigma Aldrich) in 1 mL MES buffer was prepared and 5 µL were added to each sample. Samples were then incubated on a vortex, inducing a light shake, for 15 minutes.

Following the EDC incubation, samples were centrifuged at 9000 rpm for 3 minutes and aspirated. A wash with 100 µL of MES buffer followed, with centrifugation again at 9000 rpm. An antigen solution was prepared at a concentration of 34.4 µg/mL in carbonate-bicarbonate buffer (pH 9.4). The antigens used were hepatitis B surface antigen (HBsAg, Advanced Immunochemical, Long Beach, Calif.), non-structural protein 4 (NSP4, Advanced Immunochemical) and glycoprotein 41 (gp41, Advanced Immunochemical) for hepatitis B virus (HBV), hepatitis C virus (HCV) and human immunodeficiency virus (HIV), respectively. The diluted antigen stock solutions were added to the samples to a final volume of 100 µL followed by a 15 minute incubation on a vortex.

After incubation with antigen solution, samples were centrifuged at 6500 rpm for 3 minutes, then aspirated. The QdotBs were then resuspended in 100 μL of quenching buffer (50 mM Glycine and 0.1% Tween) and incubated for another 15 minutes on a vortex. Following this incubation, samples were centrifuged at 5500 rpm for 3 minutes, aspirated and resuspended in 100 μL of 3% milk in phosphate buffer saline (PBS). A subsequent incubation on a vortex for 30 minutes served to block the QdotBs with milk proteins. Finally, the QdotBs were washed one more time with TRIS wash buffer (pH 8.0), using centrifugation at 5000 rpm. This sample could be stored dry over night if necessary.

Stock solutions of target antibody solutions were then prepared in human serum. For HBV, clone X12 anti-HBsAg was used (Advanced Immunochemical), for HCV clone 8A1 anti-HCV NS-4 was used (Biodesign International, Saco, Me.) and for HIV, clone 5A1 anti-HIV-1 gp41 was used (Biodesign International). The Antigen-coated QdotBs were resuspended in spiked human serum samples to a final volume of 100 μL. They were then incubated on a vortex for 15 minutes, followed by two washes using TRIS wash buffer, centrifuging samples at 5000 rpm.

A stock solution of AlexaFluor-488 dye conjugated goat anti-mouse IgG antibodies (Invitrogen, Burlington, ON) was diluted 1:300 in TRIS wash buffer. 100 μL of this solution was used to resuspend each sample. Samples were covered in tinfoil (to prevent organic dye photobleaching) and placed on a vortex for 15 minutes. Two final washes of the QdotB-complexes using 100 μL of TRIS wash buffer were completed before resuspending the samples in 500 μL of TRIS wash buffer for short term storage.

Assay Preparation

For the multiplexed assays, antigen-coated QdotBs were prepared as described above. All experiments used approximately the same number of total beads during antibody capture. If there were two types of antigen QdotBs being used, then half the microbeads in a sample corresponded to one code, while the rest corresponded to the other. The same method was used for samples that used three different QdotBs.

For the incubation of QdotBs with target antibody-spiked human serum, a total volume of 100 μL, was always used. Therefore, if a sample was incubated with two different targeting antibodies, then 50 μL of each spiked serum solution were added. Similarly, if three different targeting antibodies were to be incubated, 33 μL of each solution were added.

FIG. 12 lists which antigen-coated QdotBs were incubated with which target antibody-spiked human serum samples. For control (no target antibody) samples, human serum with no target antibodies was added instead. The rest of the target antibody capture assay followed the methods described above.

Microchip Fabrication

As discussed above, microchannel fabrication followed standard soft lithography techniques—e.g., as described in Y. Xia, G. M. Whitesides, Annu. Rev. Mater. Sci., 28, 153 (1998); D. C. Duffy, J. C. McDonald, O. J. A. Schueller, G. M. Whitesides, Anal. Chem., 70, 4974 (1998); and M. A. Unger, H. Chou, T. Thorsen, A. Scherer, S. R. Quake, Science, 288, 113 (2000).

Photomasks of the desired microchannel pattern were prepared using AutoCAD software (San Rafael, Calif.) and printed on a transparency by the Photoplot Store (Colorado Springs, Colo.). The resolution of the print was 1.59 μm (the distance between two pixels). Fabrication of the masters began by spin coating a 15 μm thick layer of 2015 series SU8 photoresist (MicroChem Corp., Newton, Mass.) on 3.5 inch diameter Si wafers (Virginia Semiconductor, Fredericksburg, Va.) and prebaking the samples. Each wafer then had the photomask laid on top of the photoresist, ink surface down, and was exposed to 365 nm UV light at a power density of 35 mW/cm2 for a duration of ~4 seconds using a SUSS MA6 mask aligner (SUSS MicroTec Inc., Waterbury Center, Vt.). Following standard postbaking procedures, the wafers were immersed in SU8 Nanodeveloper (MicroChem Corp.) for ~1 minute to dissolve away any photoresist not exposed to the UV light. The masters were then washed with isopropanol and dried with compressed N2 gas.

The polydimethylsiloxane (PDMS) prepolymer kits (RTV 615, General Electric Silicones, Wilton, Conn.) used come in two parts; part A is the prepolymer; part B contains a cross-linker. Prepolymer was mixed in a 10A:1B ratio. Masters were placed in pyrex Petri dishes and 22 g of prepolymer was poured on top of each. The samples were then placed under vacuum for ~2 hrs to degas (remove bubbles from) the prepolymer. A 3-hour incubation followed in an oven set at 80° C. Once removed from the oven, the cured PDMS slabs were peeled off the masters and excess polymer around the outside of the microchannel pattern was removed. A single master had patterns for two polymer microchannels. The surfaces of the PDMS substrates and glass coverslips (170 μm thick, VWR, Mississauga, ON) were then carefully cleaned using scotch tape. Both PDMS substrates and glass coverslips were loaded into the chamber of a plasma cleaner (Harrick Plasma, Ithaca, N.Y.) and exposed to oxygen plasma for 1 min. Immediately after, the surfaces of the PDMS and coverslips were brought into contact to irreversibly seal the two substrates together. Double distilled water was dispensed into the microchannels to keep the channel surfaces hydrophilic. Finally, small pieces of glass were placed on top of the channel wells to keep the water from evaporating, enabling long term storage of the samples.

Detection Experiments

First, QdotB complexes in 500 μL of TRIS wash buffer were centrifuged at 4000 rpm for 3 minutes and aspirated. They were then resuspended in 30 μL of double distilled water.

Microchannels were flushed with double distilled water once before use, by filling the buffer and waste wells and applying suction at the sample well using a custom tool. Fluid was removed from all wells prior to the introduction of sample into the chip. 20 μL of sample were loaded into the sample well, followed by 20 μL of double distilled water into each of the buffer and waste wells. The microfluidic chip was then aligned on the stage of an inverted epiflourescent microscope (IX71, Olympus, Center Valley, Pa.) and immersion oil was applied to the lens of a 60× objective (1.35 NA, Olympus). The objective lens was brought into focus at the entrance of the sample well.

Electrodes were placed in each of the wells, leads connected to the outputs of a voltage regulation circuit (see FIG. S2). The input of the voltage regulation circuit was connected to a high voltage power supply (CZE1000R, Spellman High Voltage Electronics Corp., Hauppauge, N.Y.), which supplied 300V and 60 μA to the regulation circuit during a typical experiment. The voltage ratio between the buffer and sample channels was set at 1.8.

Once QdotB complexes started to flow into the microchannel 206 as described above, the objective lens focus was moved to align with the sample focusing stream located downstream from the intersection 230 of the buffer channel 208 and sample channel 206. The objective lens 330 was then used to focus a laser spot, measuring ~8 μm in diameter and using the 488 nm Ar laser 310 line from a multi-line, Ar/Kr gas laser (COHERENT Inc., Santa Clara, Calif.) in TEM00 mode, on the ~10 µm wide single-file sample stream 140. The laser power was set at a constant 25 mW. A dichroic mirror (U-N41001, Olympus) and 500 nm longpass emission filter 320 (7512, Chroma Technology Corp., Rockingham, Vt.) were used to separate the excitation light 302 from the collected fluorescence 304. Fluorescence emission 304 was separated into spectral bands using dirchroic mirrors (q555lp and 610dlp, Chroma Technology Corp.) and bandpass filters 440a-d before being focused on the active areas of solid-state photo detectors 410a-d (see FIG. 3A).

Figure 6A:
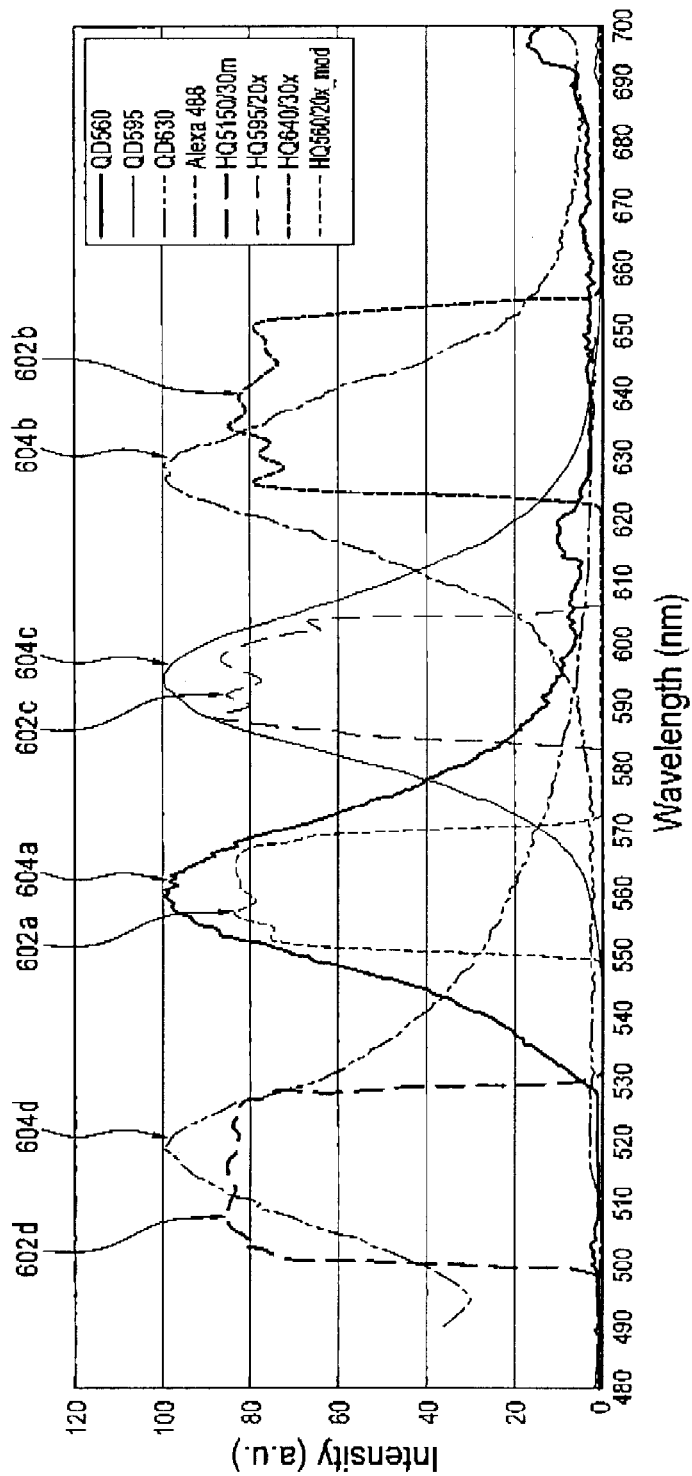
FIG. 6A is a spectrum of the quantum dots and bandpass filters used in the experiments described herein.
Figure 6B:
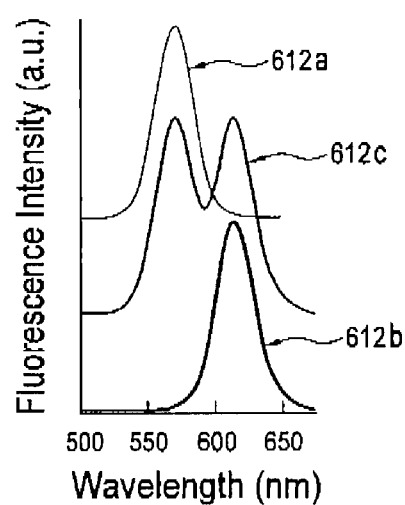
FIG. 6B is a spectrum of the quantum dots of FIG. 5B.
Figure 7A:
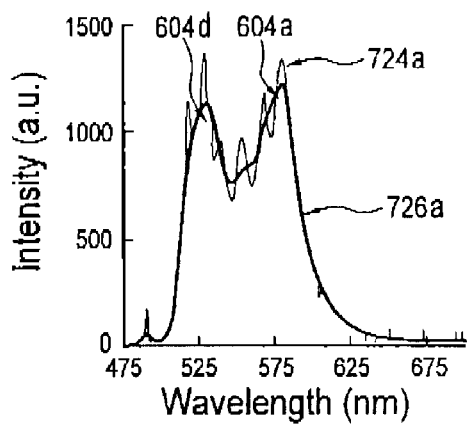
FIG. 7A is a graph of raw and fitted fluorescent emission wavelength data for the BRM conjugate of FIG. 1A.
Figure 7B:
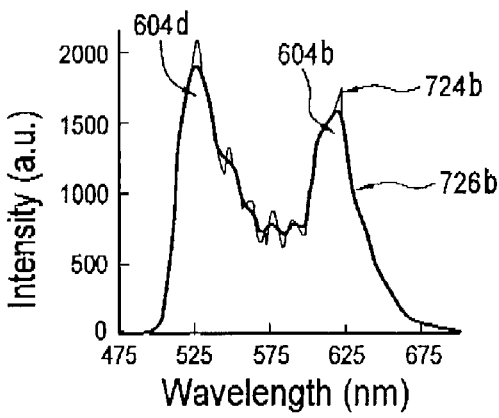
FIG. 7B is a graph of raw and fitted fluorescent emission wavelength data for the BRM conjugate of FIG. 1B.
Figure 7C:
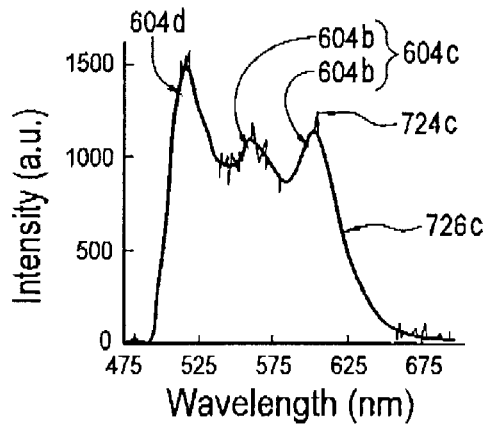
FIG. 7C is a graph of raw and fitted fluorescent emission wavelength data for the BRM conjugate of FIG. 1C.

The spectra of the Qdots and bandpass filters used is displayed in FIG. 6A. A comparison of the spectral peaks for the red, yellow and orange QdotBs is displayed in FIG. 6B. For green range wavelengths, shown as peaks 602d for the filter, and 604d for the raw fluorescence, a 500-540 nm bandpass filter 440a (HQ520/40, Chroma Technology Corp.) was used with a bi-convex lens (LB1761-A, Thorlabs Inc., Newton, N.J.) to focus these emissions on a PIN photodiode detector 410a (818 Series, Newport Corp., Irvine, Calif.). This detector was connected to an optical power meter (1830-C, Newport Corp.). Similarly, bandpass filters 440b and 440d (HQ575/30 and HQ630/60, Chroma Technology Corp.) and lenses (LB1811-A and LA1027-A, respectively, Thorlabs Inc.) were used for two avalanche photodiodes (C4777-01 and C5460 for yellow and red channels, respectively, Hamamatsu Corp., Bridgewater, N.J.). The yellow range of wavelengths are shown as peaks 602a for the filter, and 604a for the raw fluorescence and the red range of wavelengths are shown as peaks 602b for the filter, and 604b for the raw fluorescence. Voltage outputs for all three detectors were connected to ports of a data acquisition card (NI USB-6251, National Instruments, Austin, Tex.) that was relayed to a computer and operated using Labview software (National Instruments). Sampling at 1 kHz was used, though the capabilities of the data acquisition card are on the order of 1 MS/s. for comparison, FIG. 6A also shows the orange range of wavelengths as peaks 602c for the filter (see above) and 604c for the raw Qdot spectrum. The spectra for the red 612b, yellow 612a and orange 612c QdotB complexes are overlaid in FIG. 6B for comparison purposes.

A typical experiment ran for 15 minutes, allowing the collection of ~30 MB of data and ~1000 detection events. After an experiment, the QdotB complexes remaining in the sample channel were collected and counted using a cell counter (Vi-Cell XR, Beckman-Coulter, Fullerton, Calif.) and the microchannel was discarded using appropriate disposal techniques. QdotB complex concentrations in the sample well were 1.5×107/mL (9×106 standard deviation) during a typical experiment.

Collection of Spectra Using a CCD Array Camera

The collection of spectra such as those shown in FIGS. 7A-C used similar steps to those given above. Fluorescence emission, however, was directed towards and focused on the entrance slit of a spectrograph (Acton Research Inc., Acton, Mass.) using a 50.0 mm focal length lens (LA1131-A, Thorlabs Inc.). Inside the spectrograph a grating with 150 grooves per mm was used to disperse the emission light by wavelength before illuminating the pixels of a thermo-electrically cooled CCD camera (7481-0002, Princeton Instruments, Trenton, N.J.). The selection of this grating allowed inspection of the spectrum from ~450-700 nm when aligned for a central wavelength of 570 nm. The integration time of the CCD array was 50 msec, set by a mechanical shutter, while typical readout time was ~250 msec. Data taken by the camera was collected and analyzed using WinSpec software (Princeton Instruments). By collecting multiple, successive spectra, it was possible to discriminate background and detection signals from each other. The raw data for the HBV, HIV and HCV samples are shown as 724a, 724b and 724c, respectively, with fitted curves matched to the raw data as distinct fluorescent spectra 726a, 726b and 726c, respectively. The respective fitted curves show yellow peaks 604a, red peaks 604b, which combine for orange peak 604c. The green peak 604d for the target fluorophore is also present.

Theory

Downstream of the sample and buffer channels, the channel undergoes flow focusing. Flow focusing is an important aspect of the technology since microbeads in the flow tend to non-specifically adsorb onto the PDMS which can greatly affect the Qdot-barcode measurements. With flow focusing, the Qdot-barcode interaction with the PDMS substrate is minimized.

The size and shape of the channels in the microfluidic chip is determined by the size of the beads and conjugates being detected. A 5 µm bead, for example, requires approximately 7-8 µm of space to flow after functionalization and conjugation, therefore a focused flow channel no larger 10 µm in width allows for regular flow of the beads, while only permitting one beads to pass through the channel at a time.

The configuration of the channels is optimized to permit the focused flow microbeads to travel past the detection point one at a time, while maintaining the flow rate such that there is no clumping or agglomeration. The configuration depends on several factors, including the voltage applied to the focusing channel, the voltage applied to the sample channel, and the length of the various channels.

The velocity of beads is determined by:

$$V = -\frac{\varepsilon * \zeta_{eof}}{\mu}E + \frac{\varepsilon * \zeta_{eph}}{\mu}E \quad (1)$$

Where E: electrical field; ε: electrical permittivity, $\zeta_{eof}$: zeta potential of the channel wall; µ: viscosity of the fluid. $\zeta_{eph}$: zeta potential of the bead surface.

$$\frac{\varepsilon * \zeta}{\mu}$$

is also called mobility of the flow.

The mobility of the flow $$\frac{\varepsilon * \zeta}{\mu}$$

is determined by the buffer and channel wall material, ε, ξ, µ have a relationship with buffer solution's pH, temperature and other characteristics. From Equation (1) above it is shown that the microbead velocity has to be >0 to build a stable flow, which sets the criteria for selecting the buffer.

The voltage ratio (not absolute voltage) of the focusing channel to the sample channel (at the sample well) α=$U_f/U_i$ is subject to $$\alpha_{min} \leq \alpha \leq \alpha_{max} \quad (2)$$

Where $\alpha_{min}$ and $\alpha_{max}$ are related to the length of each part of the channel.

$$\alpha_{min} = \frac{\beta}{\beta+\gamma}; \alpha_{max} = 1 + \frac{1}{2\beta}.$$

and where $$\beta = \frac{L_o}{L_{f1} + L_{f2}};$$

$$\gamma = \frac{L_i}{L_{f1} + L_{f2}}.$$

$L_o$, $L_i$, $L_f$ are the length of the outlet, inlet and focusing channel, respectively. As the focusing channel in the preferred chip design has an L-shape, $L_f$ is defined as the sum of $L_{f1}$ and $L_{f2}$, the two arms of the channel.

Theoretically, there is no limitation for voltage applied to one of the channels (focusing or sample). As shown in Equation (1), flow velocity is proportional to the voltage, such that a higher voltage results in a larger flow velocity. However, there is limitation for the voltage ratio as shown in equation (2). Beyond this range, the flow cannot be generated.

Thus, the ratio of the focused width, $W_f$ of the sample flow, is related to the width of the inlet channel according to the equation:

$$W_f/W = (1 + 2 \cdot \beta \cdot \alpha)/(1 + 2 \cdot \gamma \cdot \alpha) \quad (3)$$

In the sample chip used, $L_i = 8$ mm, $L_o = 10$ mm, $L_{f1} + L_{f2} = 18$ mm. Thus, for a $W = 100$ μm channel, for various values of $\alpha$:

$\alpha = 1.5$: $W_f/W = 0.19$, $W_f = 19$ μm
$\alpha = 1.6$: $W_f/W = 0.14$, $W_f = 14$ μm
$\alpha = 1.7$: $W_f/W = 0.09$, $W_f = 9$ μm
$\alpha = 1.8$: $W_f/W = 0.04$, $W_f = 4$ μM
with $\alpha_{max} = 1.93$; $\alpha_{min} = 0.59$.

The formulas above are based on the assumption that all the channels are straight, with no convergence and divergence, and the height is the same for all branches. If the assumption is incorrect, the formula will change, but will obey the same principles as outlined. In addition, there is no limitation for the length of each branch, as different length combinations will merely result in different widths for the focused fluid.

Data Analysis

Figure 8B:
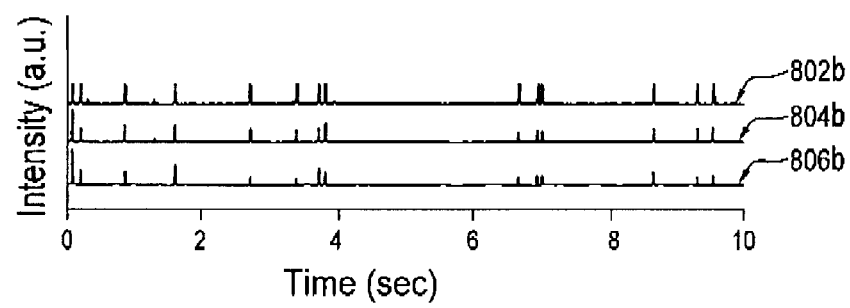
FIG. 8B is a graph of intensity vs. time measurements for the BRM conjugates of FIG. 1B.
Figure 8C:
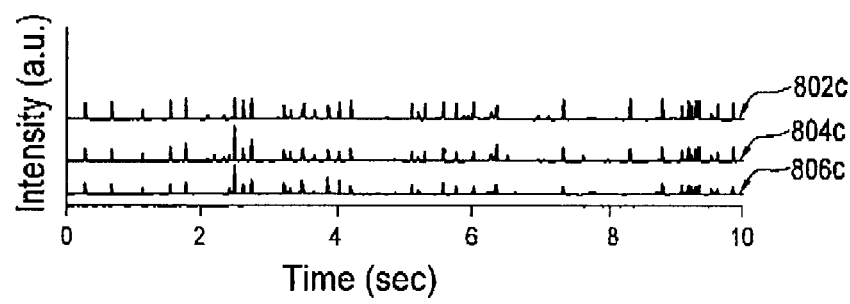
FIG. 8C is a graph of intensity vs. time measurements for the BRM conjugates of FIG. 1C.

FIGS. 8A-C and show 10-second intervals of raw data collected during experiments where large fluctuations in detector output voltages indicate detection events in real time. For these experiments, a PIN photodiode coupled to an optical power meter and amplifier was used to examine green (500-540 nm) wavelengths 802*a-c*, corresponding to the target fluorophore part of the spectrum, shown as 604*d* in FIG. 7A-C, while APDs were used for yellow 804*a-c* and red channels 806*a-c* (550-590 nm and 600-650 nm, respectively), which correspond to the BRM part of the spectrum shown as 604*a-c* in FIGS. 7A-C. Outputs from all three detectors were linked to a computer using a data acquisition card and run using Labview software. Since the speed that a barcode traverses the laser spot is inversely proportional to the peak intensity measured by a detector, normalized voltage peak values with respect to time were used for signal analysis. For example, the green channel, which indicates target antibody detection, used the metric $G = \int^{peak} V(t) dt / \int^{peak} dt$, where $V(t)$ is the voltage signal as a function of time, t. FIG. 9 provides a close-up of a series of peak to demonstrate the range of voltages.

Figure 10A:
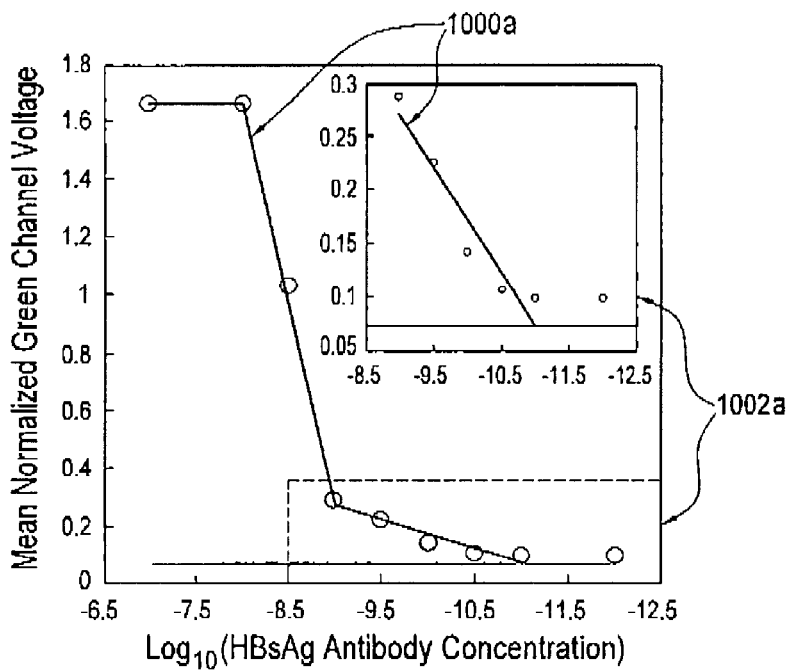
FIG. 10A is a graph of intensity vs. concentration measurements for the BRM conjugates of FIG. 1A.
Figure 10B:
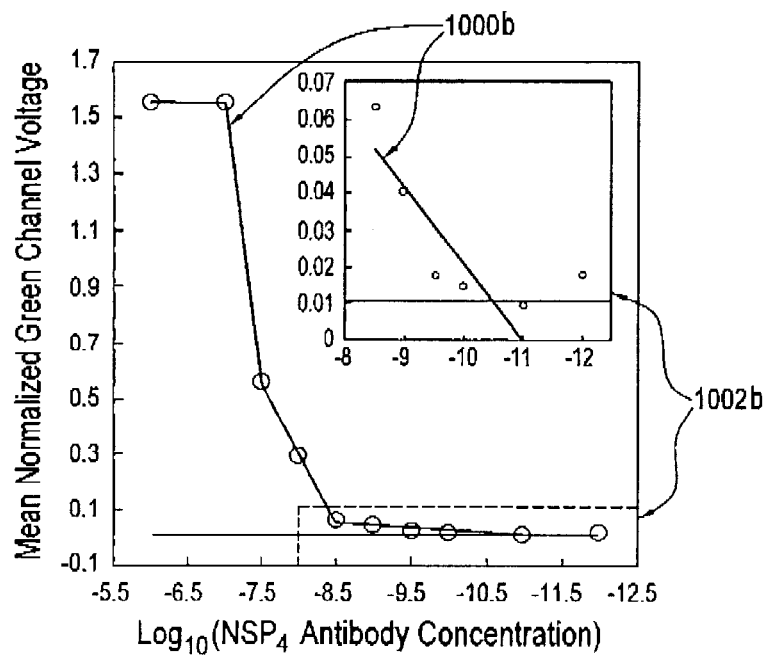
FIG. 10B is a graph of intensity vs. concentration measurements for the BRM conjugates of FIG. 1A.
Figure 10C:
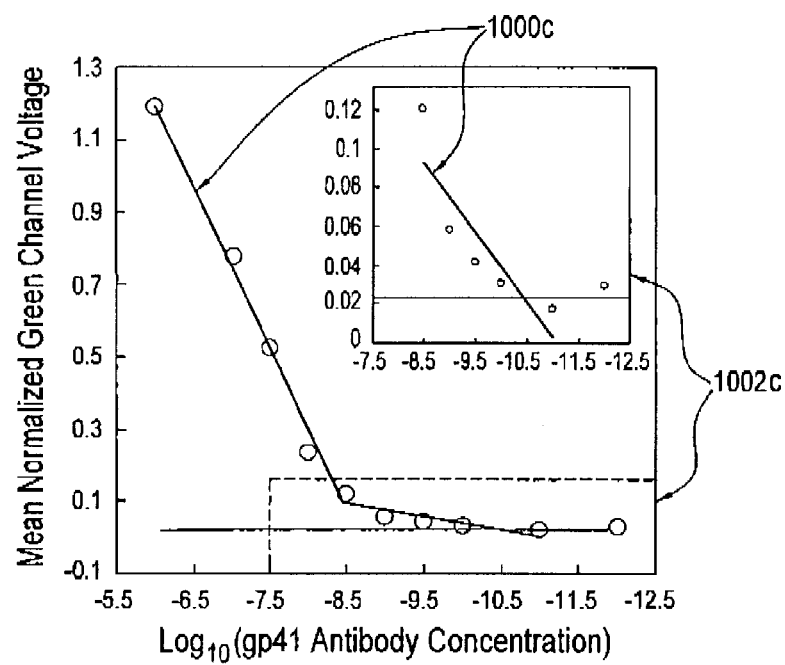
FIG. 10C is a graph of intensity vs. concentration measurements for the BRM conjugates of FIG. 1A.

False positives are a common clinically encountered problem for assays being performed at target molecule levels approaching the detection sensitivity limit of the diagnostic. Therefore, assessing the detection limit for the platform is important and serial dilution sensitivity curves for HBV HBsAg, HCV $NSP_4$ and HIV gp41 target antibodies were prepared and compared to commercially available ELISA kits. The detection algorithm first scanned the green channel for peaks and then made sure appropriate peaks were also present in the yellow and red channels before a detection event was confirmed. The values for detection peaks are plotted in FIGS. 10A-C. Log curves 1000*a*, 1000*b* and 1000*c* are respectively fitted to data for HBV, HIV and HCV, with expanded views 1002*a*, 1002*b* and 1002*c* respectively showing addition detail at the tail end of the curves. For HBsAg antibodies, the detection sensitivity limit was measured in the femtomolar ($10^{-13}$-$10^{-15}$M) range, while the limits for $NSP_4$ and gp41 were on the picomolar scale ($10^{-10}$-$10^{-12}$M).

The required bead concentration is based on the need to measure the single bead signal; high bead concentrations require higher speed detectors and data acquisition systems. Bead to bead interactions become a factor due to the small separation between beads, which will affect flow. For low bead concentrations, it will take longer to generate enough counts for statistical analysis (over 1000 in the current experiment). The average bead concentration is $15 \times 10^6$ m/L with a standard deviation of $9 \times 10^6$ m/L in the examples shown, taking approximately 15 minutes to get >1000 counts. The range of acceptable concentration is thus estimated between $15 \times 10^7$ m/L and $15 \times 10^5$ m/L, with a corresponding change in the time required for count acquisition. The actual size of the beads can range from as a little as 100 nm up to 5 μm.

Figure 11A:
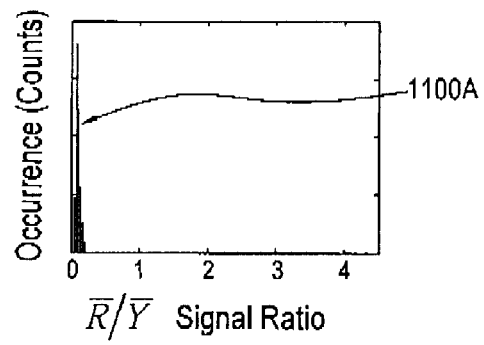
FIG. 11A is a histogram of R/Y signal ratios for the BRM conjugates of FIG. 1A.
Figure 11B:
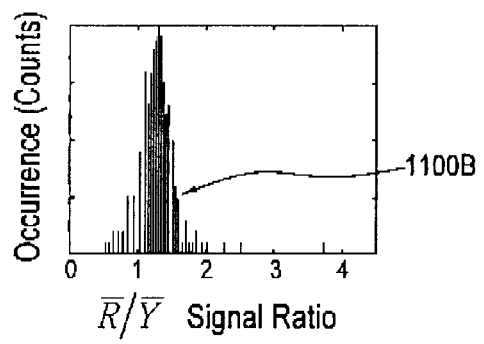
FIG. 11B is a histogram of R/Y signal ratios for the BRM conjugates of FIG. 1B.
Figure 11C:
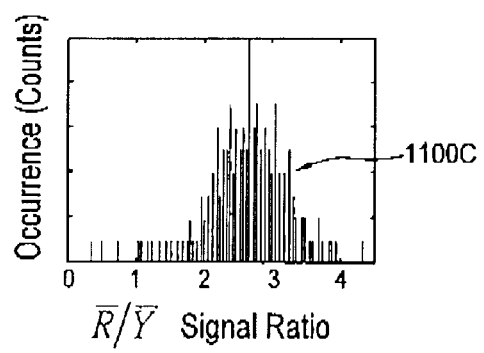
FIG. 11C is a histogram of R/Y signal ratios for the BRM conjugates of FIG. 1C.
Figure 11D:
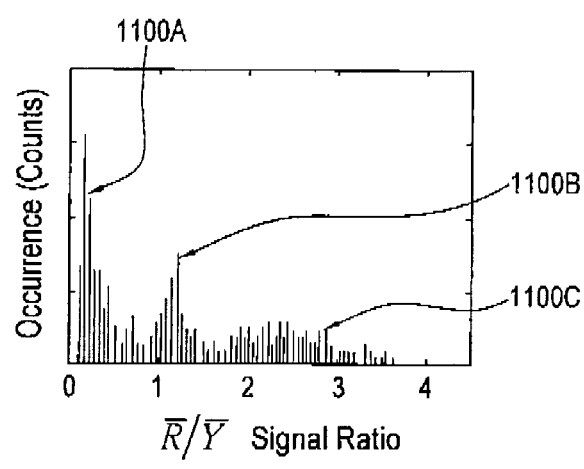
FIG. 11D is a merged histogram of FIGS. 11A, 11B, and 11C.

A major benefit of using fluorescent barcodes is their multiplexing detection capacity and the ability to apply it to pathogen detection. FIGS. 11A-D, 12 and 13A-B show results of two (HBV and HIV) and three (HBV, HCV and HIV) pathogen multiplexing experiments. The detector data was analyzed by first indicating where green channel peaks were present, and then classified as HBV, HCV or HIV detection events based on the ratio of normalized values R/Y. FIGS. 11A-C show how histograms 1100*a*, 1100*b*, 1100*c* of detection events from HBV, HIV and HCV have clearly distinguishable differences in the R/Y ratios, from low to medium to high, respectively, with a comparison of all three in FIG. 11D. By using this approach, it was possible to identify the different pathogen detection events in the same sample, and when the target molecules present during the assay were modified, the results accounted for this change.

Figure 13A:
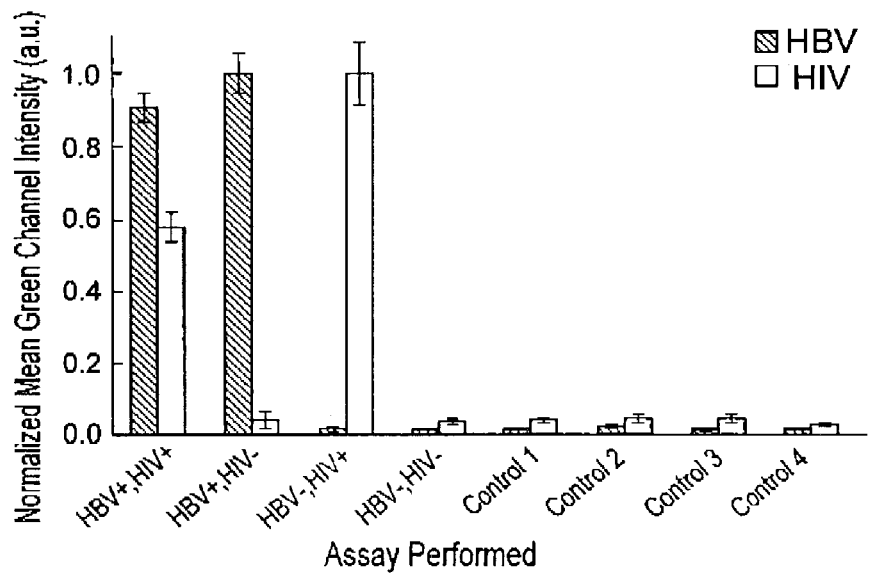
FIG. 13A is a graph of 2-pathogen multiplexing results.
Figure 13B:
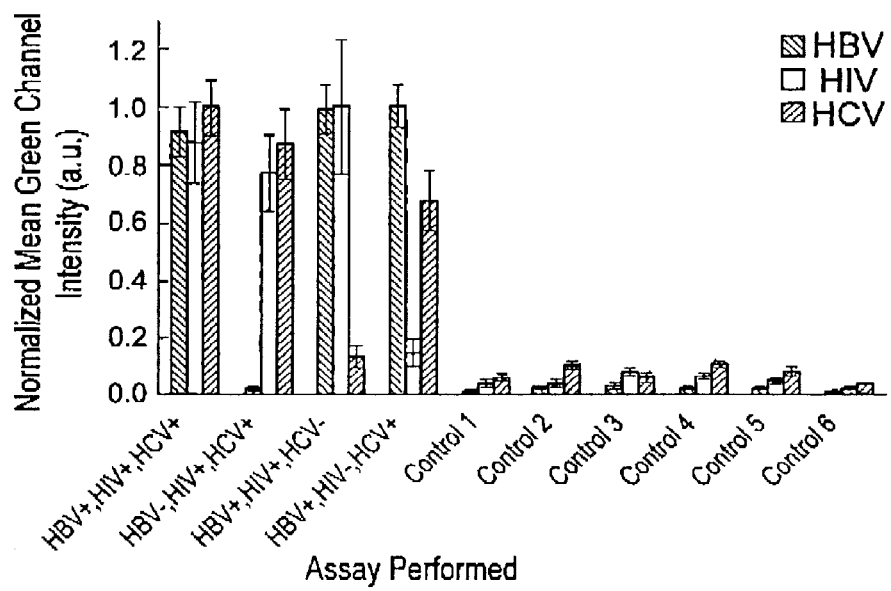
FIG. 13B is a graph of 3-pathogen multiplexing results.

FIG. 12 shows a table of experiments used for FIGS. 13A and 13B). FIG. 13A shows the results of 2 pathogen multiplexing experiments with HBV and HIV. FIG. 13B shows the results of 3 pathogen multiplexing experiments with HBV, HCV and HIV. These results show negligible cross-reactivity for these three pathogen markers. Concentrations of HBV, HIV, and HCV antibodies for this experiment were all 4.74× 10−9 M. The error bars shown represent one standard deviation.

The microfluidic detection system represents a successful convergence of nano- and microtechnologies with molecular diagnostics into a multiplexed infectious disease bioanalytical tool. Certain modifications can be made to the system to adapt it for detection of specific molecules or use with specific antibodies. Other modification can be made to adjust the size and structure of the overall system incorporating the microfluidic chip. For example, an LED or other radiation emitting element may be used in place of the laser for the purpose of exciting the molecules. Further developments and refinements, not all of which will be readily obvious to those skilled in the art, may present themselves.

While the above method has been presented in the context of a quantum dot-based barcode the method is equally applicable to fluorescent dyes and other types of luminescent particles.

This concludes the description of a presently preferred embodiment of the invention.

What is claimed is:

1. A test system for use with a buffer to test for the presence of target molecules of one or more target types in a biological test sample, the test system comprising:
   (a) a first set of detection molecules, each comprising one or more biorecognition molecules (BRMs) immobilized relative to one or more BRM fluorophores, wherein each of the BRMs is specific for one of the target types, so as to form conjugates of the BRMs and the target molecules, if present in the test sample, with the conjugates comprising one or more conjugate types each corresponding to a different one of the detection molecules in conjugation with its specific one of the target types;
   (b) a microfluidic chip comprising a chip substrate portion shaped to define:
      (i) one or more elongate sample channels therein sized to enable passage therethrough of the conjugates; and
      (ii) one or more flow focusing channels therein for operative passage therethrough of the buffer, with the one or more flow focusing channels adjoining the one or more elongate sample channels, with the buffer exiting from the flow focusing channels operatively directing a single-file stream of the conjugates through at least one of the sample channels;
   (c) an irradiating device operatively delivering electromagnetic frequency (EMF) radiation, at an irradiation position along said at least one of the sample channels, for absorption by the conjugates in the single-file stream, wherein the conjugates emit fluorescence after absorption of the EMF radiation, and wherein the fluorescence of the conjugates comprises a distinct fluorescent spectrum for each one of the conjugate types; and
   (d) a detection device monitoring the single-file stream for the fluorescence emitted by the conjugates, wherein the detection device identifies the presence of the conjugates by monitoring for the distinct fluorescent spectrum of each one of the conjugate types;
   wherein each of the detection molecules further comprises a microbead directly or indirectly coupled to, and substantially interposed between, the BRMs and the BRM fluorophores, wherein each of the conjugates further comprises a target marker fluorophore bound to a respective one of the target molecules, and wherein for each of the conjugates, the BRM fluorophores emit a BRM part, and the target marker fluorophore emits a target part, of the fluorescence of the distinct fluorescent spectrum after absorption of the EMF radiation, such that the BRM fluorophores and the target marker fluorophore together emit the fluorescence of the distinct fluorescent spectrum after absorption of the EMF radiation; and
   whereby the test system identifies the presence of the target molecules in the test sample.

2. The test system according to claim 1, wherein the BRM fluorophores comprise one or more quantum dots, with the quantum dots comprising one or more quantum dot types, and wherein the quantum dots together emit at least said BRM part of the fluorescence of the distinct fluorescent spectrum after absorption of the EMF radiation.

3. The test system according to claim 2, wherein the quantum dots comprise two or more of the quantum dot types.

4. The test system according to claim 1, wherein the BRM fluorophores comprise one or more fluorescent dyes, with the fluorescent dyes comprising one or more fluorescent dye types, and wherein the fluorescent dyes together emit at least said BRM part of the fluorescence of the distinct fluorescent spectrum after absorption of the EMF radiation.

5. The test system according to claim 1, wherein the conjugates are less than about 10 micrometers (µm) in size.

6. The test system according to claim 5, wherein the conjugates are less than about 5 µm in size.

7. The test system according to claim 6, wherein the conjugates are less than about 1 µm in size.

8. The test system according to claim 1, wherein each of the conjugates further comprises a target marker fluorophore bound to a respective one of the target molecules, and wherein the target marker fluorophore emits a target part of the fluorescence of the distinct fluorescent spectrum after absorption of the EMF radiation.

9. The test system according to claim 1, wherein the detection device comprises at least two avalanche photodetectors (APDs) monitoring the single-file stream for the fluorescence emitted by the conjugates, with a first one of the APDs adapted to receive and identify the presence of the BRM part, and a second one of the APDs adapted to receive and identify the presence of the target part, of the fluorescence of the distinct fluorescent spectrum for said each of the conjugates.

10. The test system according to claim 9, wherein the target part has a lower intensity than the BRM part of the fluorescence of the distinct fluorescent spectrum for said each of the conjugates, and wherein the second one of the APDs has a greater sensitivity than the first one of the APDs.

11. The test system according to claim 1, wherein said at least one of the sample channels is defined by one or more elongate channel walls of the chip substrate portion, with the channel walls comprising two opposing side channel portions, and wherein the buffer exiting from the flow focusing channels operatively directs the single-file stream of the conjugates along a sample path that is in spaced relation from at least the two opposing side channel portions.

12. The test system according to claim 11, wherein the microfluidic chip further comprises a glass slide underlying the chip substrate portion, with the glass slide defining a bottom channel portion of said at least one of the sample channels, wherein the channel walls further comprise a top channel portion, and wherein the sample path is operatively positioned in said spaced relation from both the bottom channel portion and the top channel portion.

13. The test system according to claim 1, wherein said at least one of the sample channels comprises a sample focused channel, with the sample channels further comprising a sample supply channel in fluid communication with the sample focused channel, and with the sample focused channel being downstream of the flow focusing channels, such that the buffer exiting from the flow focusing channels and the single-file stream of the conjugates operatively flow through the sample focused channel.

14. The test system according to claim 13, wherein a buffer flow rate of the buffer in the sample focused channel is higher than a test flow rate of the conjugates in the single-file stream.

15. The test system according to claim 1, wherein the flow focusing channels comprise at least two flow focusing channels, adjoining the one or more elongate sample channels upstream of said at least one of the sample channels, with the two flow focusing channels adjoining the one or more elongate sample channels from opposing sides of said at least one of the sample channels.

16. The test system according to claim 15, wherein the two flow focusing channels adjoin the one or more elongate sample channels at a common intersection portion.

17. The test system according to claim 16, wherein the buffer exiting from the flow focusing channels operatively focuses the conjugates into the single-file stream by less than about 10 micrometers (μm) downstream of the common intersection portion.

18. The test system according to claim 1, wherein each of the one or more flow focusing channels adjoins the one or more elongate sample channels at an adjoining angle of about 90 degrees.

19. The test system according to claim 1, wherein each of the one or more flow focusing channels adjoins the one or more elongate sample channels at an adjoining angle of about 45 degrees.

20. The test system according to claim 1, wherein the chip substrate portion is fabricated from polydimethylsiloxane (PDMS).

21. The test system according to claim 1, wherein passage of the conjugates through said at least one of the sample channels is facilitated by electrokinetic flow.

22. The test system according to claim 21, wherein the flow focusing channels are in fluid communication with the sample channels; wherein the chip substrate portion is further shaped to define a buffer well adjacent a buffer starting point of each one of the flow focusing channels, a sample well adjacent a sample starting point of the sample channels upstream of the flow focusing channels, and a terminal well adjacent an end point of said at least one of the sample channels downstream of the flow focusing channels; wherein the test system further comprises a sample well electrode operatively positioned in the sample well, a buffer well electrode operatively positioned in each said buffer well, and a terminal well electrode operatively positioned in the terminal well; wherein the sample well electrode is operatively supplied with a first electrical potential of a first polarity; wherein the terminal well electrode is operatively supplied with a second electrical potential of an opposing second polarity; and wherein each said buffer well electrode is operatively supplied with a third electrical potential of the first polarity.

23. The test system according to claim 22, wherein the third electrical potential is higher than the first electrical potential.

24. The test system according to claim 23, wherein a ratio of the third electrical potential relative to the first electrical potential is about 1.8:1.

25. The test system according to claim 1, wherein a test flow rate of the conjugates in the single-file stream is at least about 30 conjugates per minute.

26. The test system according to claim 25, wherein the test flow rate is at least about 60 conjugates per minute.

27. The test system according to claim 26, wherein the test flow rate is about 500 conjugates per minute.

28. The test system according to claim 1, wherein the irradiating device comprises a light emitting diode (LED) operatively emitting the EMF radiation for absorption by the conjugates in the single-file stream.

29. The test system according to claim 1, wherein the irradiating device comprises a laser operatively emitting the EMF radiation for absorption by the conjugates in the single-file stream.

30. The test system according to claim 29, wherein the laser has an operating power of between about 2 megawatts (mW) and about 50 megawatts (mW).

31. The test system according to claim 30, wherein the operating power of the laser is between about 20 megawatts (mW) and about 25 megawatts (mW).

32. The test system according to claim 1, wherein the EMF radiation operatively delivered by the irradiating device has an EMF wavelength of about 488 nm.

33. The test system according to claim 1, wherein the detection device comprises three or more avalanche photodetectors (APDs) monitoring the single-file stream for the fluorescence emitted by the conjugates, with each of the APDs adapted to receive and identify the presence of a different range of wavelengths in the fluorescence emitted by the conjugates.

34. The test system according to claim 33, wherein a first one of the APDs is adapted to receive and identify the presence of a green range of wavelengths, wherein a second one of the APDs is adapted to receive and identify the presence of a yellow range of wavelengths, and wherein a third one of the APDs is adapted to receive and identify the presence of a red range of wavelengths.

35. The test system according to claim 33, wherein a first one of the APDs is adapted to receive and identify the presence of a green range of wavelengths, wherein a second one of the APDs is adapted to receive and identify the presence of a yellow range of wavelengths, wherein a third one of the APDs is adapted to receive and identify the presence of an orange range of wavelengths, and wherein a fourth one of the APDs is adapted to receive and identify the presence of a red range of wavelengths.

36. The test system according to claim 33, wherein a first one of the APDs is adapted to receive and identify the presence of a blue range of wavelengths, wherein a second one of the APDs is adapted to receive and identify the presence of a green range of wavelengths, wherein a third one of the APDs is adapted to receive and identify the presence of a yellow range of wavelengths, and wherein a fourth one of the APDs is adapted to receive and identify the presence of a red range of wavelengths.

37. The test system according to claim 1, wherein the detection device comprises a charge-coupled device monitoring the single-file stream for the fluorescence emitted by the conjugates.

38. The test system according to claim 1, wherein the detection device comprises at least two avalanche photodetectors (APDs) monitoring the single-file stream for the fluorescence emitted by the conjugates, with each of the APDs adapted to receive and identify the presence of a different range of wavelengths in the fluorescence emitted by the conjugates; wherein the detection device further comprises a charge-coupled device monitoring the single-file stream for the fluorescence emitted by the conjugates; and wherein the detection device still further comprises a switch means for switching between monitoring the single-file stream with either the APDs or the charge-coupled device.

39. The test system according to claim 1, wherein the detection device comprises at least one trip sensor monitoring the single-file stream for the fluorescence emitted by the conjugates, with each said trip sensor generating a digital signal corresponding to an intensity of the fluorescence.

40. The test system according to claim 39, wherein each said trip sensor generates the digital signal only when the intensity of the fluorescence is in excess of a minimum intensity, and wherein each said trip sensor has a different predetermined said minimum intensity.

41. The test system according to claim 1, further comprising a fiber optic cable, with the fiber optic cable operatively delivering the fluorescence to the detection device from substantially adjacent to the irradiation position along said at least one of the sample channels.

42. The test system according to claim 1, further comprising a housing encasing the irradiating device and the detection device, with the housing sized and adapted for portable and point-of-care diagnostic use.

43. The test system according to claim 42, wherein the housing is sized and adapted for hand-held use.

44. The test system according to claim 1, wherein a buffer flow rate of the buffer in the sample focused channel is higher than a test flow rate of the conjugates in the single-file stream.

45. The test system according to claim 1, wherein the test system is particularly adapted for use with one or more biological test samples selected from the group consisting of blood, urine, sputum, and serum.

46. A test system to test for the presence of target molecules of one or more target types in a biological test sample, with the test system being for use with:
- a first set of detection molecules, each comprising one or more biorecognition molecules (BRMs) immobilized relative to one or more BRM fluorophores, wherein each of the BRMs is specific for one of the target types, so as to form conjugates of the BRMs and the target molecules, if present in the test sample, with the conjugates comprising one or more conjugate types each corresponding to a different one of the detection molecules in conjugation with its specific one of the target types, with the conjugates emitting fluorescence after absorption of electromagnetic frequency (EMF) radiation; and
- a microfluidic chip comprising a chip substrate portion shaped to define one or more elongate sample channels therein sized to enable passage therethrough of the conjugates, with a single-file stream of the conjugates passing through at least one of the sample channels;
- wherein each of the detection molecules further comprises a microbead directly or indirectly coupled to, and substantially interposed between, the BRMs and the BRM fluorophores, wherein each of the conjugates further comprises a target marker fluorophore bound to a respective one of the target molecules, and wherein for each of the conjugates, the BRM fluorophores emit a BRM part, and the target marker fluorophore emits a target part, of the fluorescence of the distinct fluorescent spectrum after absorption of the EMF radiation, such that the BRM fluorophores and the target marker fluorophore together emit the fluorescence of the distinct fluorescent spectrum after absorption of the EMF radiation; and wherein the test system comprises:
(a) an irradiating device operatively delivering the EMF radiation, at an irradiation position along said at least one of the sample channels, for absorption by the conjugates in the single-file stream, wherein the conjugates emit fluorescence after absorption of the EMF radiation, and wherein the fluorescence of the conjugates comprises a distinct fluorescent spectrum for each one of the conjugate types; and
(b) a detection device monitoring the single-file stream for the fluorescence emitted by the conjugates, wherein the detection device identifies the presence of the conjugates by monitoring for the distinct fluorescent spectrum of each one of the conjugate types;

whereby the test system identifies the presence of the target molecules in the test sample.

* * * * *